(12) United States Patent
Chowdhury

(10) Patent No.: US 11,268,959 B2
(45) Date of Patent: *Mar. 8, 2022

(54) BOVINE HERPESVIRUS DETECTION AND TREATMENT

(71) Applicant: Shafiqul Islam Chowdhury, Baton Rouge, LA (US)

(72) Inventor: Shafiqul Islam Chowdhury, Baton Rouge, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 43 days.

This patent is subject to a terminal disclaimer.

(21) Appl. No.: 16/896,985

(22) Filed: Jun. 9, 2020

(65) Prior Publication Data

US 2021/0011017 A1   Jan. 14, 2021

Related U.S. Application Data

(63) Continuation of application No. 15/501,094, filed as application No. PCT/US2015/043112 on Jul. 31, 2015, now Pat. No. 10,690,669.

(60) Provisional application No. 62/032,098, filed on Aug. 1, 2014.

(51) Int. Cl.
*G01N 33/569* (2006.01)

(52) U.S. Cl.
CPC ... *G01N 33/56983* (2013.01); *G01N 2333/03* (2013.01)

(58) Field of Classification Search
None
See application file for complete search history.

(56) References Cited

U.S. PATENT DOCUMENTS

| 4,036,945 | A | 7/1977 | Haber |
| 4,331,647 | A | 5/1982 | Goldenberg |
| 5,747,654 | A | 5/1998 | Pastan et al. |
| 6,221,360 | B1 | 4/2001 | Chowdhury |
| 6,284,251 | B1 * | 9/2001 | Chowdhury ............ A61P 37/04 424/199.1 |
| 10,690,669 | B2 * | 6/2020 | Chowdhury ..... G01N 33/56983 |
| 2002/0019517 | A1 | 2/2002 | Koide |
| 2005/0244814 | A1 | 11/2005 | Esty et al. |
| 2012/0269728 | A1 | 10/2012 | Jen et al. |

(Continued)

FOREIGN PATENT DOCUMENTS

| EP | 154204 A2 | 9/1985 |
| WO | 92/21751 A1 | 12/1992 |
| WO | 2016/019244 A1 | 2/2016 |

OTHER PUBLICATIONS

Sequence alignment of instant SEQ ID 1 with U.S. Appl. No. 10/690,669 SEQ ID Jun. 1, 2020.*

(Continued)

*Primary Examiner* — Shanon A. Foley
(74) *Attorney, Agent, or Firm* — Venable LLP; Keith G. Haddaway

(57) ABSTRACT

Methods, compositions, devices, and kits are described herein that are useful for detecting BoHV-1 infection in animals and/or for distinguishing animals that may benefit from administration of BoHV-1 tmv vaccine.

19 Claims, 14 Drawing Sheets

Specification includes a Sequence Listing.

(56) References Cited

U.S. PATENT DOCUMENTS

| | | | |
|---|---|---|---|
| 2014/0079704 A1* | 3/2014 | Mwangi | A61K 35/761 424/136.1 |
| 2019/0086406 A1 | 3/2019 | Chowdhury | |

OTHER PUBLICATIONS

Sequence alignment of instant SEQ ID 4 with U.S. Appl. No. 10/690,669 SEQ ID Jun. 4, 2020.*
Extended European Search Report dated Dec. 8, 2020 in corresponding European Application No. EP20193609.3.
El-Kholy et al., "Baculovirus expression and diagnostic utility of the glycoprotein E of bovine herpesvirus-1.1 Egyptian strain "Abu-Hammad"", Journal of Virological Methods, Jul. 1, 2013, vol. 191, No. 1, pp. 33-40.
Letellier et al., "Characterization of monoclonal antiodies directed against the bovine herpesvirus-1 glycoprotein E and use for the differentiation between vaccinated and infected animals", Veterinary Microbiology, Dec. 1, 2001, vol. 83, No. 4, pp. 301-315.
Rijsewijk et al., "Epitopes on glycoprotein E and on the glycoprotein E/glycoprotein I complex of bovine herpesvirus 1 are expressed by all of 222 isolates and 11 vaccine strains", Archives of Virology, May 1, 2000, vol. 145, No. 5, pp. 921-936.
Wellenberg et al., "Antibodies against bovine herpesvirys (BHV) 5 may be differentiated from antibodies againsst BHV1 in a BHV1 glycoprotein E blocking ELISA", Verterinary Microbiology, Jan. 1, 2001, vol. 78, No. 1, pp. 79-84.
An, "Binary Ti Vectors for Plant Transformation and Promoter Analysis", Methods in Enzymology (1987), vol. 153, pp. 292-305.
Bork et al., "The immunoglobulin fold Structural classification, sequence patterns and common core", J. Mol. Biol., (1994), vol. 242, pp. 309-320.
Bork et al., Proposed acquisition of an animal protein domain by bacteria, Proc. Natl. Acad. Sci. USA, (Oct. 1992), vol. 89, pp. 8990-8994.
Brum et al., "Bovine herpesvirus type 1 (BoHV-1) anterograde neuronal transport from trigeminal ganglia to nose and eyes requires glycoprotein E", J Neurovirol., (2009), vol. 15, pp. 196-201.
Butchi et al., "Envelope protein Us9 is required for the anterograde transport of bovine herpesvirus type 1 from trigeminal ganglia to nose and eye upon reactivation", J Neurovirol., (2007), vol. 13, pp. 384-388.
Campbell et al., "Building proteins with fibronectin type III modules", Structure, (May 15, 1994), vol. 2, pp. 233-337.
Chandler et al., "Two Regulatory Genes of the Maize Anthocyanin Pathway Are Homologous: Isolation of B Utilizing R Genomic Sequences", The Plant Cell, (Dec. 1989), vol. 1, pp. 1175-1183.
Chowdhury et al., "A bovine herpesvirus type 1 mutant virus with truncated glycoprotein E cytoplasmic tail has defective anterograde neuronal transport in rabbit dorsal root ganglia primary neuronal cultures in a microfluidic chamber system", J. Neurovirol., (2010), vol. 17, pp. 457-465.
Chowdhury et al., "A triple gene mutant of BoHV-1 administered intranasally is significantly more efficacious than a BoHV-1 glycoprotein E-deleted virus against a virulent BoHV-1 challenge", Vaccine, (2014), vol. 32, pp. 4909-4915.
Chowdhury, "Construction and characterization of an attenuated bovine herpesvirus type-1 (BHV-1) recombinant", Veterinary Microbiology, (1996), vol. 52, pp. 13-23.
Clackson et al., "In vitro selection from protein and peptide libraries", Trends Biotechnol., (May 1994), vol. 12, pp. 173-184.
Ebert et al., "Identification of an essential upstream element in the nopaline synthase promoter by stable and transient assays", Proc. Natl. Acad. Sci. USA., (1987), vol. 84, pp. 5745-5749.
Harpaz et al., "Many of the Immunoglobulin Superfamily Domains in Cell Adhesion Molecules and Surface Receptors Belong to a New Structural Set Which is Close to That Containing Variable Domains", J. Mol. Biol., (1994), vol. 238, pp. 528-539.
Hudspeth et al., "Structure and expression of the maize gene encoding the phosphoenolpyruvate carboxylase isozyme involved in C4 photosynthesis", Plant Molecular Biology, (1989), vol. 12, pp. 579-589.
Jones et al., "A Review of the Biology of Bovine Herpesvirus Type 1 (BHV-1), Its role as a Cofactor in the Bovine Respiratory Disease Complex and Development of Improved Vaccines", Anim Health Res Rev., (2007), vol. 8, No. 2, pp. 187-205.
Jones et al., "Bovine herpesvirus type 1 (BHV-1) is an Important Cofactor in the Bovine Respiratory Disease Complex", Vet Clin North Am Food Anim Pract, (2010), vol. 26, pp. 303-321.
Jones, "The immunoglobulin superfamily", Curr. Opinion Struct. Biol., (1993), vol. 3, pp. 846-852.
Kaashoek et al., "Virulence, immunogenicity and reactivation of seven bovine herpesvirus 1.1 strains: Clinical and virological aspects", Vet Rec., (1996), vol. 139, pp. 416-421.
Kohler et al., "Continuous cultures of fused cells secreting antibody of predefined specificity", Nature, (Aug. 7, 1975), vol. 256, pp. 495-497.
Koppers-Lalic et al., "Varicelloviruses avoid T cell recognition by UL49.5-mediated inactivation of the transporter associated with antigen processing", Proc Natl Acad Sci USA, (2005), vol. 102, No. 14, pp. 5144-5149.
Kozbor et al., "The production of Monoclonal antibodies from human lymphocytes", Immunol Today, (1983), vol. 4, No. 3, pp. 72-79.
Lawton et al., "Expression of a soybean ?-conclycinin gene under the control of the Caulitflower Mosaic Virus 35S and 19S promoters in transformed petunia tissues", Plant Molecular Biology, (1987), vol. 9, pp. 315-324.
Lipinska et al., "Bovine Herpesvirus 1 UL 49.5 Protein Inhibits the Transporter Associated with Antigen Processing despite Complex Formation with Glycoprotein M", J Virol 80, (2006), vol. 12, pp. 5822-5832.
Liu et al., "A Bovine Herpesvirus Type 1 Mutant Virus Specifying a Carboxyl-Terminal Truncation of Glycoprotein E is Defective in Anterograde Neuronal Transport in Rabbits and Calves", J Virol., (2008), vol. 82, No. 15, pp. 7432-7442.
Lowman et al., "Selecting High-Affinity Binding Proteins by Monovalent Phage Display", Biochemistry (1991), vol. 30, pp. 10832-10838.
Nataraj et al., "Bovine Herpesvirus 1 Downregulates the Expression of Bovine MHC Class I Molecules", Viral Immunol., (1997), vol. 10, No. 1, pp. 21-34.
Niedz et al., "Green fluorescent protein: an in vivo reporter of plant gene expression", Plant Cell Reports, (1995), vol. 14, pp. 403-406.
Odell et al., "Identification of DNA sequences required for activity of the cauliflower mosaic virus 35S promoter", Nature, (Feb. 28, 1985), vol. 313, pp. 810-812.
O'Neil et al., "Phage Display of Random Peptides on a Protein Scaffold", Techniques in Protein Chemistry V (Crabb, L,. ed.) (1994), pp. 517-524, Academic Press, San Diego.
Ow et al., "Transient and Stable Expression of the Firefly Luciferase Gene in Plant Cells and Transgenic Plants", Science, (Nov. 14, 1986), vol. 234, No. 4778, pp. 856-859.
Pal et al., "Nanowire labeled direct-charge transfer biosensor for detecting *Bacillus* species", Biosensors and Bioelectronics, (2007), vol. 22, pp. 2329-2336.
Potrykus et al., "Direct gene transfer to cells of a graminaceous monocot". Mol. Gen. Genet., (1985), vol. 199, pp. 183-188.
Prasher et al., "Cloning and Expression of the cDNA Coding for Aequorin, a Bioluminescent Calcium-Binding Protein", Biochem. Biophys. Res. Comm., (Feb. 15, 1985), vol. 126, No. 3, pp. 1259-1268.
Roberts et al., "Directed evolution of a protein: Selection of potent neutrophil elastase inhibitors displayed on M13 fusion phage", PNAS, (Mar. 1992), vol. 89, pp. 2429-2433.
Sullivan et al., "Isolation and Charactierization of a maize chlorophyll a/b binding protein gene that produces high levels of mRNA in the dark", Mol. Gen. Genet., (1989), vol. 215, pp. 431-440.
Thillet et al., "Site-directed Mutagenesis of Mouse Dihydrofolate Reductase", J. Biol. Chem., (Sep. 5, 1988), vol. 263, No. 25, pp. 12500-12508.

(56) References Cited

OTHER PUBLICATIONS

Tikoo et al., "Bovine Herpesvirus 1 (BHV-1): Biology, Pathogenesis, and Conrol", Adv Virus Res., (1995), vol. 45, pp. 191-223.
Venturini et al., "Phage Display of the Minibody: A ?-Scaffold for the Selection of Conformationally-Contrained Peptides", Protein Peptide Letters, (1994), vol. 1, No. 1, pp. 70-75.
Walker et al., "DNA sequences required for anaerobic expression of the maize alcohol dehydrogenase 1 gene", Proc. Natl. Acad. Sci. USA., (1987), vol. 84, pp. 6624-6628.
Wang et al., "Characterization of cis-Acting Elements Regulating Transcription from the Promoter of a Constitutively Active Rice Actin Gene", Mol. Cell. Biol., (Aug. 1992), vol. 12, No. 8, pp. 3399-3406.
Wei et al., "Bovine Herpesvirus Type 1 (BHV-1) UL 49.5 Luminal Domain Residues 30 to 32 Critical for MHC-1 Down-Regulation in Virus-Infected Cells", PloS one, (Oct. 2011), vol. 6, Issue 10, (11 pages).
Yang et al., "Maize sucrose synthase-1 promoter directs phloem cell-specific expression of Gus gene in transgenic tobacco plants", Proc. Natl. Acad. Sci. USA., (1990), vol. 87, pp. 4144-4148.
European Application Serial No. 15753250.8, Communication Pursuant to Article 94(3) EPC dated Dec. 6, 2017 (5 pages).
European Application Serial No. 15753250.8, Communication pursuant to Rules 161(1) and 162 EPC dated Mar. 10, 2017 (8 pages).
European Application Serial No. 15753250.8, Response filed Sep. 19, 2017 to Communication pursuant to Rules 161(1) and 162 EPC dated Mar. 10, 2017 (12 pages).
International Application Serial No. PCT/US2015/043112, International Preliminary Report on Patentability dated Feb. 16, 2017 (8 pages).
International Search Report and Written Opinion issued in International Application No. PCT/US2015/043112 dated Oct. 12, 2015, (4 pages).
Sequence alignment of SEQ ID No. 1 with Geneseq db access No. AAR30045 by Rijsewijk et al. in WO92/21751 Dec. 1992.

\* cited by examiner

```
  1  ASQKRTYDIL  NPFGPVYTSL  PTNEPLDVVV  PVSDDEFSLD
 41  EDSFADDDSD  DDGPASNPPA  DAYDLAGAPE  PTSGFARAPA
 81  NGTRSSRSGF  KVWFRDPLED  DAAPARTPAA  PDYTVVAARL
121  KSILR
```

Fig. 1B

```
  1  GCATCGCAAA  AGCGTACCTA  TGATATTCTG  AACCCGTTTG
 41  GTCCGGTCTA  CACGAGCCTG  CCGACGAACG  AACCGCTGGA
 61  TGTTGTTGTG  CCTGTTAGTG  ATGACGAATT  TTCCCTGGAT
121  GAAGACTCAT  TCGCCGATGA  CGATTCGGAC  GATGACGGTC
161  CGGCAAGCAA  CCCGCCGGCA  GATGCTTATG  ATCTGGCAGG
201  TGCACCGGAA  CCGACCTCTG  GTTTTGCACG  TGCTCCGGCG
241  AATGGCACGC  GTAGCTCTCG  CTCCGGTTTT  AAAGTCTGGT
281  TCCGCGATCC  GCTGGAAGAT  GACGCGGCCC  CGGCGCGTAC
321  CCCGGCGGCA  CCGGACTACA  CCGTGGTTGC  GGCCCGTCTG
361  AAGAGCATCC  TGCGT
```

Fig. 1C

|  | Ndel | Poly His-Tag | | | |
|---|---|---|---|---|---|
| 1 | CATATGCATC | ACCACCATCA | CCACGCATCG | CAAAAGCGTA | CCTATGATAT | TCTGAACCCG |
| 61 | TTTGGTCCGG | TCTACGGAG | CCTGCGACG | AACGAACCGC | TGGATGTTGT | TGTGCCTGTT |
| 121 | AGTGATGACG | AATTTCCCT | GGATGAAGAC | TCATTCGCCG | ATGACGATTC | GGACGATGAC |
| 181 | GGTCCGGCAA | GCAACCGCC | GGCAGATGCT | TATGATCTGG | CAGGTGCACC | GGAACCGACC |
| 241 | TCTGGTTTTG | CACGTGCTCC | GGCGAATGGC | ACGGGTAGCT | CTCGCTCCGG | TTTTAAAGTC |
| 301 | TGGTTCCGCG | ATCCGCTGGA | AGATGACGCG | GCCCCGGGCG | GTACCCCGG | GGCACCGGAC |
| 361 | TACACCGTGG | TTGCGGCCCG | ATCCTGCGTT | AATGACTCGA | G | |
|  |  |  |  | Stop Stop | XhoI | |

Fig. 1D

```
  1       10         20         30         40         50         60
  MHHHHHHASQ KRTYDILNEF GPVYTSLPTN EPLDVYVPVS IDEFSLDEDS EADDDSDIDG 70         80         90        100        110        120
  PASNPPADAY DLAGAPEPTS GFARAPANGT RSSRSGFKVM FRDPLEDDAA PARTPAAPDY

130
TVVARLKSI LR
```

Theoretical pI/Mw: 4.59 / 14314.50

*Fig. 1E*

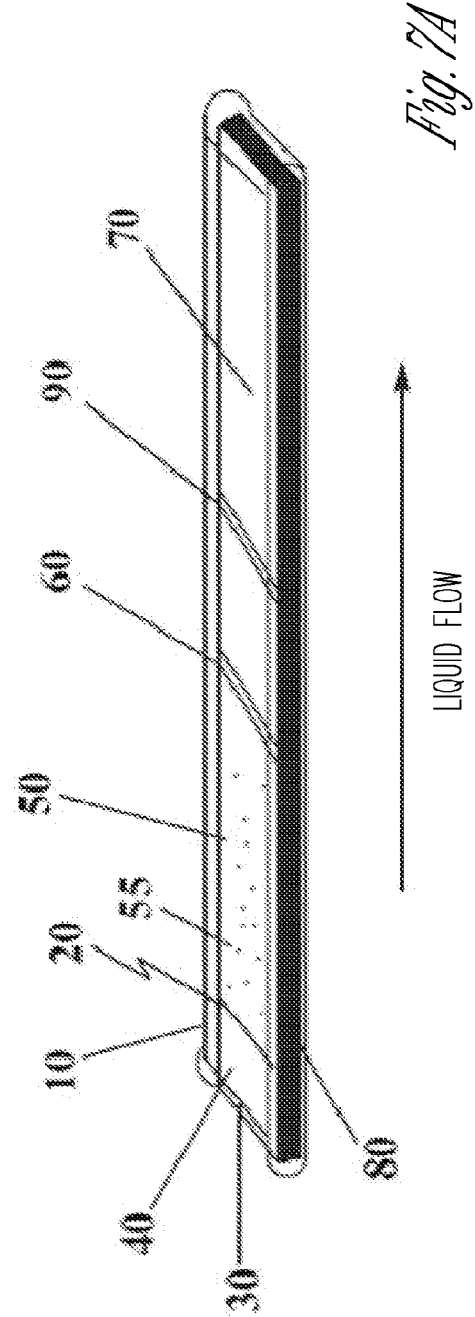
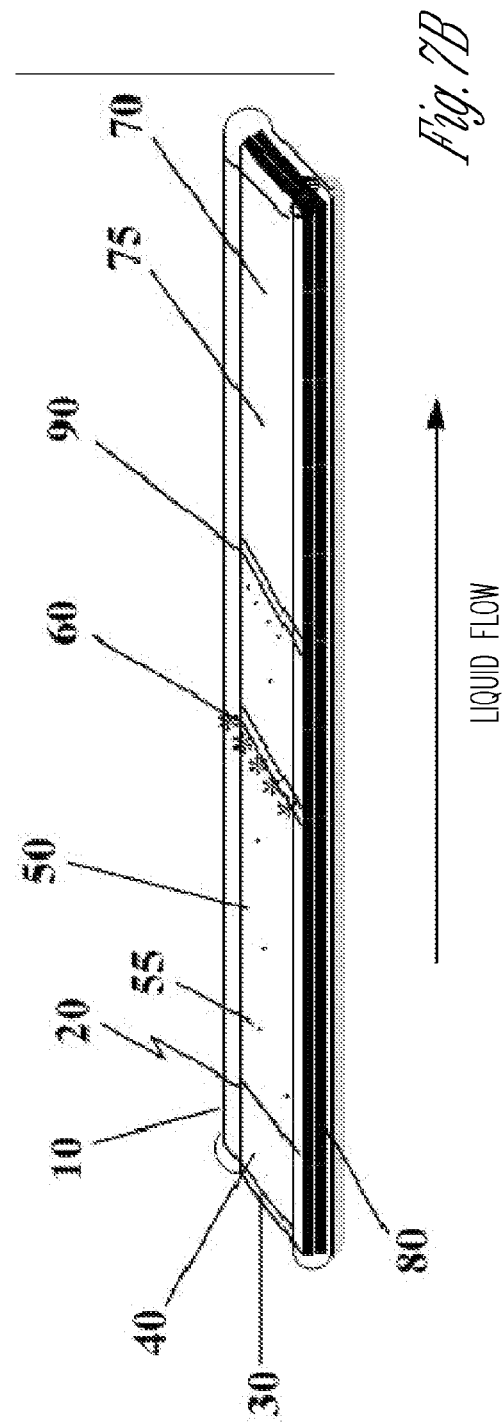

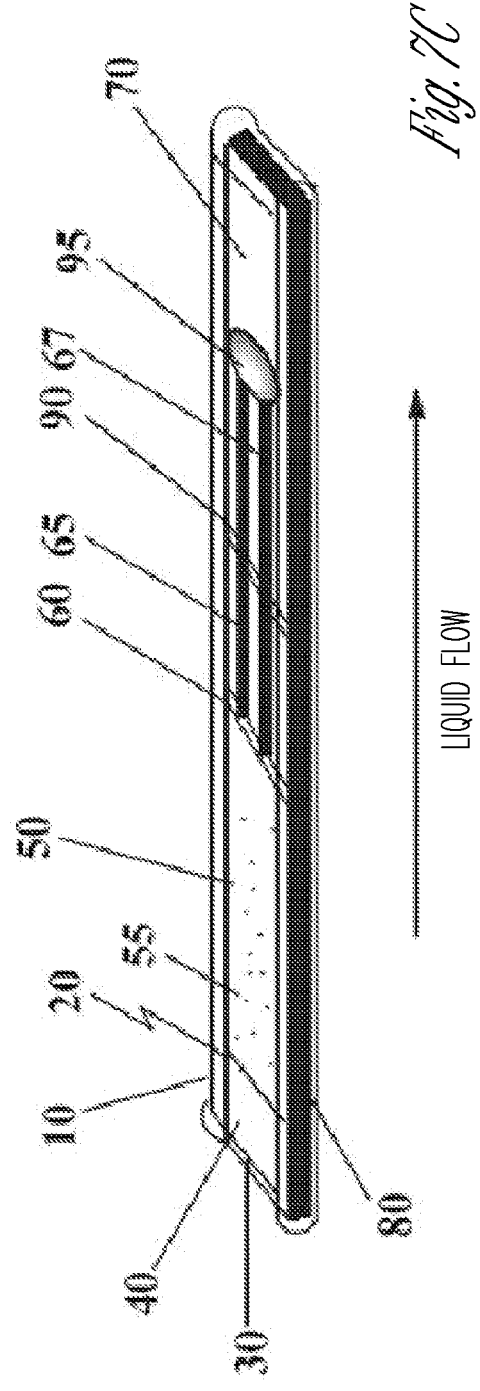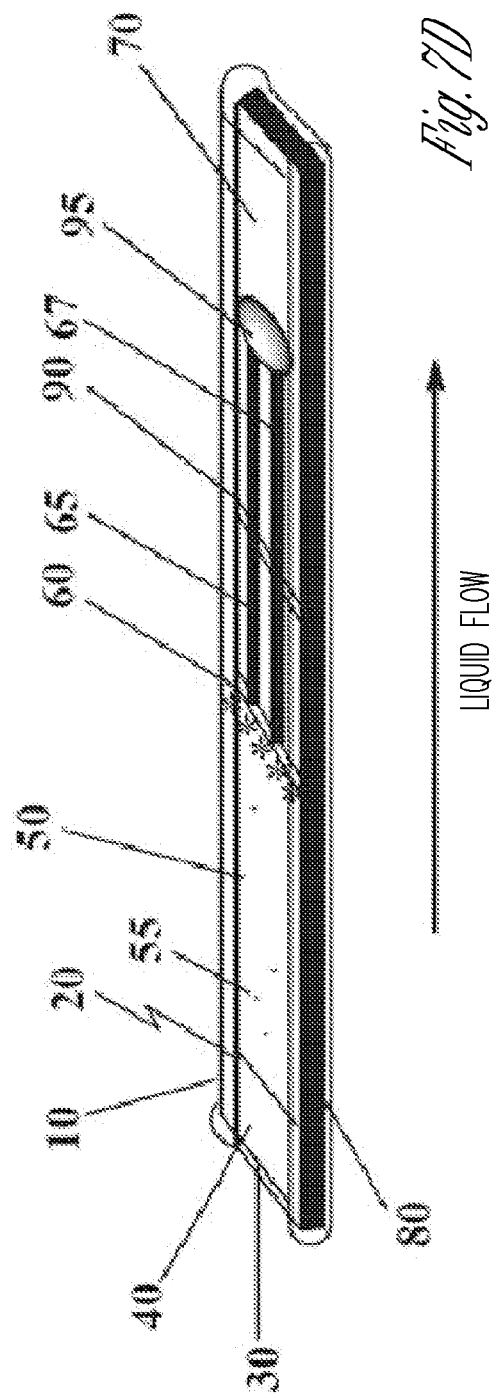

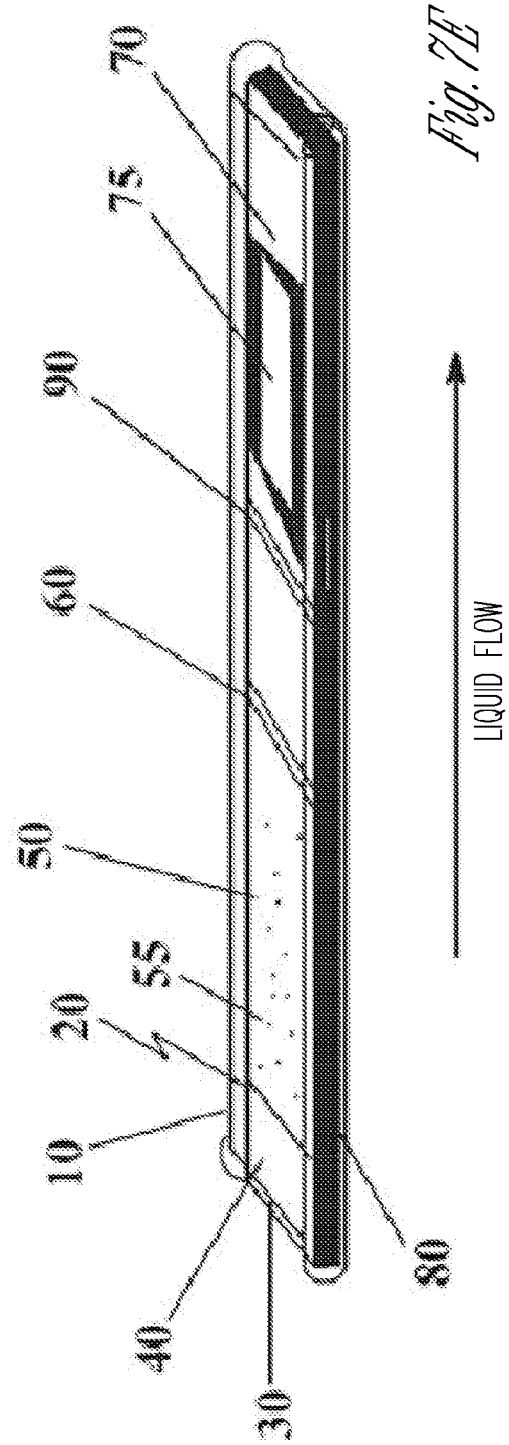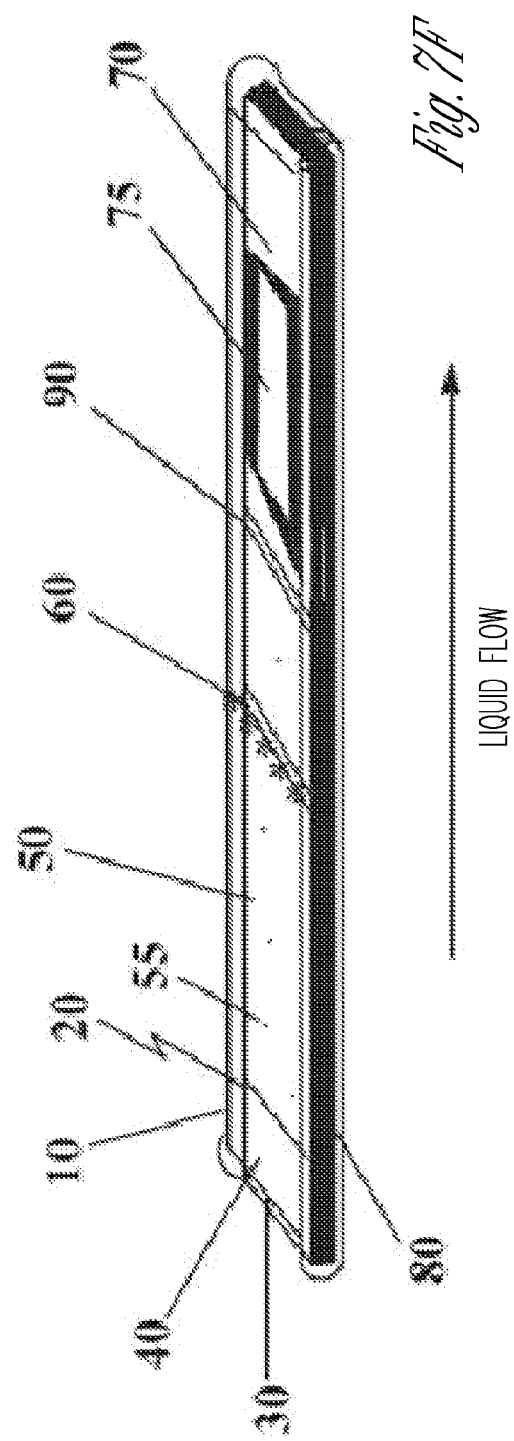

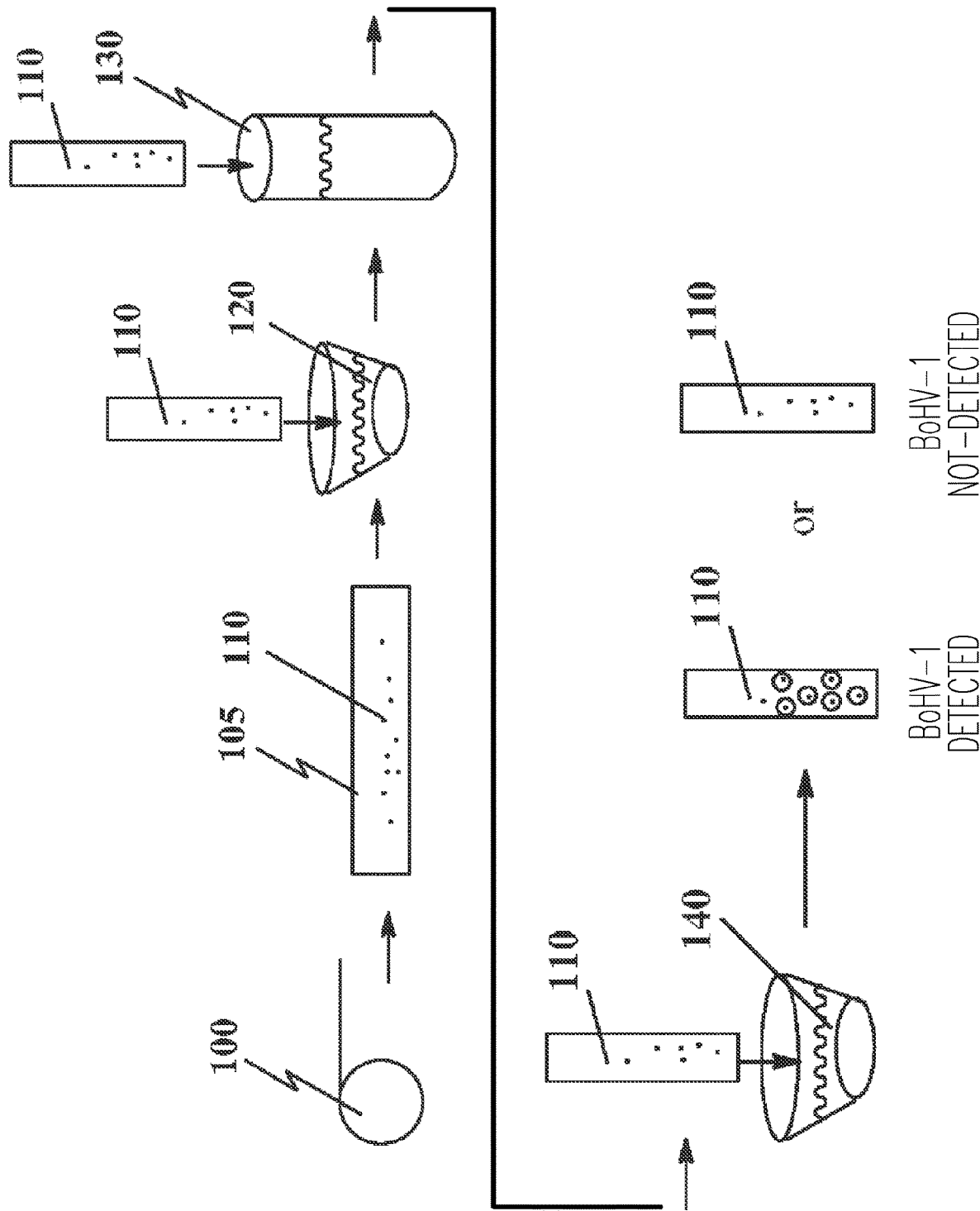

SEQUENCE LISTING

```
<160> NUMBER OF SEQ ID NOS: 45

<210> SEQ ID NO 1
<211> LENGTH: 125
<212> TYPE: PRT
<213> ORGANISM: Artificial Sequence
<220> FEATURE:
<223> OTHER INFORMATION: A synthetic polypeptide

<400> SEQUENCE: 1

Ala Ser Gln Lys Arg Thr Tyr Asp Ile Leu Asn Pro Phe Gly Pro Val
1               5                   10                  15

Tyr Thr Ser Leu Pro Thr Asn Glu Pro Leu Asp Val Val Pro Val
            20                  25                  30

Ser Asp Asp Glu Phe Ser Leu Asp Glu Asp Ser Phe Ala Asp Asp Asp
        35                  40                  45
```

Ser Asp Asp Gly Pro Ala Ser Asn Pro Pro Ala Asp Ala Tyr Asp
    50              55                  60

Leu Ala Gly Ala Pro Glu Pro Thr Ser Gly Phe Ala Arg Ala Pro Ala
65              70                  75                  80

Asn Gly Thr Arg Ser Ser Arg Ser Gly Phe Lys Val Trp Phe Arg Asp
                85                  90                  95

Pro Leu Glu Asp Asp Ala Ala Pro Ala Arg Thr Pro Ala Ala Pro Asp
            100                 105                 110

Tyr Thr Val Val Ala Ala Arg Leu Lys Ser Ile Leu Arg
            115                 120                 125

<210> SEQ ID NO 2
<211> LENGTH: 375
<212> TYPE: DNA
<213> ORGANISM: Artificial Sequence
<220> FEATURE:
<223> OTHER INFORMATION: A synthetic oligonucleotide

<400> SEQUENCE: 2
gcatcgcaaa agcgtaccta tgatattctg aacccgtttg gtccggtcta cacgagcctg      60
ccgacgaacg aaccgctgga tgttgttgtg cctgttagtg atgacgaatt ttccctggat     120
gaagactcat tcgccgatga cgattcggac gatgacggtc cggcaagcaa cccgccggca     180
gatgcttatg atctggcagg tgcaccggaa ccgacctctg gttttgcacg tgctccggcg     240
aatggcacgc gtagctctcg ctccggtttt aaagtctggt tccgcgatcc gctggaagat     300
gacgcggccc cggcgcgtac cccggcggca ccggactaca ccgtggttgc ggcccgtctg     360
aagagcatcc tgcgt                                                      375

<210> SEQ ID NO 3
<211> LENGTH: 411
<212> TYPE: DNA
<213> ORGANISM: Artificial Sequence
<220> FEATURE:
<223> OTHER INFORMATION: A synthetic oligonucleotide

<400> SEQUENCE: 3
catatgcatc accaccatca ccacgcatcg caaaagcgta cctatgatat tctgaacccg      60
tttggtccgg tctacacgag cctgccgacg aacgaaccgc tggatgttgt tgtgcctgtt     120
agtgatgacg aatttttccct ggatgaagac tcattcgccg atgacgattc ggacgatgac     180
ggtccggcaa gcaacccgcc ggcagatgct tatgatctgg caggtgcacc ggaaccgacc     240
tctggttttg cacgtgctcc ggcgaatggc acgcgtagct ctcgctccgg ttttaaagtc     300
tggttccgcg atccgctgga agatgacgcg gccccggcgc gtaccccggc ggcaccggac     360
tacaccgtgg ttgcggcccg tctgaagagc atcctgcgtt aatgactcga g              411

<210> SEQ ID NO 4
<211> LENGTH: 132
<212> TYPE: PRT
<213> ORGANISM: Artificial Sequence
<220> FEATURE:
<223> OTHER INFORMATION: A synthetic polypeptide

<400> SEQUENCE: 4

Met His His His His His His Ala Ser Gln Lys Arg Thr Tyr Asp Ile
1               5                   10                  15

Leu Asn Pro Phe Gly Pro Val Tyr Thr Ser Leu Pro Thr Asn Glu Pro
            20                  25                  30

```
Leu Asp Val Val Pro Val Ser Asp Glu Phe Ser Leu Asp Glu
         35                  40                  45

Asp Ser Phe Ala Asp Asp Ser Asp Asp Gly Pro Ala Ser Asn
 50                  55                  60

Pro Pro Ala Asp Ala Tyr Asp Leu Ala Gly Ala Pro Glu Pro Thr Ser
 65                  70                  75                  80

Gly Phe Ala Arg Ala Pro Ala Asn Gly Thr Arg Ser Arg Ser Gly
                 85                  90                  95

Phe Lys Val Trp Phe Arg Asp Pro Leu Glu Asp Ala Ala Pro Ala
                100                 105                 110

Arg Thr Pro Ala Ala Pro Asp Tyr Thr Val Val Ala Ala Arg Leu Lys
                115                 120                 125

Ser Ile Leu Arg
    130
```

<210> SEQ ID NO 5
<211> LENGTH: 12
<212> TYPE: PRT
<213> ORGANISM: Artificial Sequence
<220> FEATURE:
<223> OTHER INFORMATION: A synthetic polypeptide

<400> SEQUENCE: 5

```
Ala Ser Gln Lys Arg Thr Tyr Asp Ile Leu Asn Pro
 1               5                  10
```

<210> SEQ ID NO 6
<211> LENGTH: 12
<212> TYPE: PRT
<213> ORGANISM: Artificial Sequence
<220> FEATURE:
<223> OTHER INFORMATION: A synthetic polypeptide

<400> SEQUENCE: 6

```
Lys Arg Thr Tyr Asp Ile Leu Asn Pro Phe Gly Pro
 1               5                  10
```

<210> SEQ ID NO 7
<211> LENGTH: 12
<212> TYPE: PRT
<213> ORGANISM: Artificial Sequence
<220> FEATURE:
<223> OTHER INFORMATION: A synthetic polypeptide

<400> SEQUENCE: 7

```
Tyr Asp Ile Leu Asn Pro Phe Gly Pro Val Tyr Thr
 1               5                  10
```

<210> SEQ ID NO 8
<211> LENGTH: 12
<212> TYPE: PRT
<213> ORGANISM: Artificial Sequence
<220> FEATURE:
<223> OTHER INFORMATION: A synthetic polypeptide

<400> SEQUENCE: 8

```
Leu Asn Pro Phe Gly Pro Val Tyr Thr Ser Leu Pro
 1               5                  10
```

<210> SEQ ID NO 9
<211> LENGTH: 12
<212> TYPE: PRT
<213> ORGANISM: Artificial Sequence
<220> FEATURE:

<223> OTHER INFORMATION: A synthetic polypeptide

<400> SEQUENCE: 9

Phe Gly Pro Val Tyr Thr Ser Leu Pro Thr Asn Glu
1               5                   10

<210> SEQ ID NO 10
<211> LENGTH: 12
<212> TYPE: PRT
<213> ORGANISM: Artificial Sequence
<220> FEATURE:
<223> OTHER INFORMATION: A synthetic polypeptide

<400> SEQUENCE: 10

Val Tyr Thr Ser Leu Pro Thr Asn Glu Pro Leu Asp
1               5                   10

<210> SEQ ID NO 11
<211> LENGTH: 12
<212> TYPE: PRT
<213> ORGANISM: Artificial Sequence
<220> FEATURE:
<223> OTHER INFORMATION: A synthetic polypeptide

<400> SEQUENCE: 11

Ser Leu Pro Thr Asn Glu Pro Leu Asp Val Val Val
1               5                   10

<210> SEQ ID NO 12
<211> LENGTH: 12
<212> TYPE: PRT
<213> ORGANISM: Artificial Sequence
<220> FEATURE:
<223> OTHER INFORMATION: A synthetic polypeptide

<400> SEQUENCE: 12

Thr Asn Glu Pro Leu Asp Val Val Val Pro Val Ser
1               5                   10

<210> SEQ ID NO 13
<211> LENGTH: 12
<212> TYPE: PRT
<213> ORGANISM: Artificial Sequence
<220> FEATURE:
<223> OTHER INFORMATION: A synthetic polypeptide

<400> SEQUENCE: 13

Pro Leu Asp Val Val Val Pro Val Ser Asp Asp Glu
1               5                   10

<210> SEQ ID NO 14
<211> LENGTH: 12
<212> TYPE: PRT
<213> ORGANISM: Artificial Sequence
<220> FEATURE:
<223> OTHER INFORMATION: A synthetic polypeptide

<400> SEQUENCE: 14

Val Val Val Pro Val Ser Asp Asp Glu Phe Ser Leu
1               5                   10

<210> SEQ ID NO 15
<211> LENGTH: 12
<212> TYPE: PRT
<213> ORGANISM: Artificial Sequence
<220> FEATURE:
<223> OTHER INFORMATION: A synthetic polypeptide

<400> SEQUENCE: 15

Pro Val Ser Asp Asp Glu Phe Ser Leu Asp Glu Asp
1               5                   10

<210> SEQ ID NO 16
<211> LENGTH: 12
<212> TYPE: PRT
<213> ORGANISM: Artificial Sequence
<220> FEATURE:
<223> OTHER INFORMATION: A synthetic polypeptide

<400> SEQUENCE: 16

Asp Asp Glu Phe Ser Leu Asp Glu Asp Ser Phe Ala
1               5                   10

<210> SEQ ID NO 17
<211> LENGTH: 12
<212> TYPE: PRT
<213> ORGANISM: Artificial Sequence
<220> FEATURE:
<223> OTHER INFORMATION: A synthetic polypeptide

<400> SEQUENCE: 17

Phe Ser Leu Asp Glu Asp Ser Phe Ala Asp Asp Asp
1               5                   10

<210> SEQ ID NO 18
<211> LENGTH: 12
<212> TYPE: PRT
<213> ORGANISM: Artificial Sequence
<220> FEATURE:
<223> OTHER INFORMATION: A synthetic polypeptide

<400> SEQUENCE: 18

Asp Glu Asp Ser Phe Ala Asp Asp Ser Asp Asp
1               5                   10

<210> SEQ ID NO 19
<211> LENGTH: 12
<212> TYPE: PRT
<213> ORGANISM: Artificial Sequence
<220> FEATURE:
<223> OTHER INFORMATION: A synthetic polypeptide

<400> SEQUENCE: 19

Ser Phe Ala Asp Asp Asp Ser Asp Asp Gly Pro
1               5                   10

<210> SEQ ID NO 20
<211> LENGTH: 12
<212> TYPE: PRT
<213> ORGANISM: Artificial Sequence
<220> FEATURE:
<223> OTHER INFORMATION: A synthetic polypeptide

<400> SEQUENCE: 20

Asp Asp Asp Ser Asp Asp Asp Gly Pro Ala Ser Asn
1               5                   10

<210> SEQ ID NO 21
<211> LENGTH: 12
<212> TYPE: PRT
<213> ORGANISM: Artificial Sequence
<220> FEATURE:
<223> OTHER INFORMATION: A synthetic polypeptide

```
<400> SEQUENCE: 21

Ser Asp Asp Gly Pro Ala Ser Asn Pro Pro Ala
1               5                   10

<210> SEQ ID NO 22
<211> LENGTH: 12
<212> TYPE: PRT
<213> ORGANISM: Artificial Sequence
<220> FEATURE:
<223> OTHER INFORMATION: A synthetic polypeptide

<400> SEQUENCE: 22

Asp Gly Pro Ala Ser Asn Pro Pro Ala Asp Ala Tyr
1               5                   10

<210> SEQ ID NO 23
<211> LENGTH: 12
<212> TYPE: PRT
<213> ORGANISM: Artificial Sequence
<220> FEATURE:
<223> OTHER INFORMATION: A synthetic polypeptide

<400> SEQUENCE: 23

Ala Ser Asn Pro Pro Ala Asp Ala Tyr Asp Leu Ala
1               5                   10

<210> SEQ ID NO 24
<211> LENGTH: 12
<212> TYPE: PRT
<213> ORGANISM: Artificial Sequence
<220> FEATURE:
<223> OTHER INFORMATION: A synthetic polypeptide

<400> SEQUENCE: 24

Pro Pro Ala Asp Ala Tyr Asp Leu Ala Gly Ala Pro
1               5                   10

<210> SEQ ID NO 25
<211> LENGTH: 12
<212> TYPE: PRT
<213> ORGANISM: Artificial Sequence
<220> FEATURE:
<223> OTHER INFORMATION: A synthetic polypeptide

<400> SEQUENCE: 25

Asp Ala Tyr Asp Leu Ala Gly Ala Pro Glu Pro Thr
1               5                   10

<210> SEQ ID NO 26
<211> LENGTH: 12
<212> TYPE: PRT
<213> ORGANISM: Artificial Sequence
<220> FEATURE:
<223> OTHER INFORMATION: A synthetic polypeptide

<400> SEQUENCE: 26

Asp Leu Ala Gly Ala Pro Glu Pro Thr Ser Gly Phe
1               5                   10

<210> SEQ ID NO 27
<211> LENGTH: 12
<212> TYPE: PRT
<213> ORGANISM: Artificial Sequence
<220> FEATURE:
<223> OTHER INFORMATION: A synthetic polypeptide

<400> SEQUENCE: 27
```

Gly Ala Pro Glu Pro Thr Ser Gly Phe Ala Arg Ala
1               5                   10

<210> SEQ ID NO 28
<211> LENGTH: 12
<212> TYPE: PRT
<213> ORGANISM: Artificial Sequence
<220> FEATURE:
<223> OTHER INFORMATION: A synthetic polypeptide

<400> SEQUENCE: 28

Glu Pro Thr Ser Gly Phe Ala Arg Ala Pro Ala Asn
1               5                   10

<210> SEQ ID NO 29
<211> LENGTH: 12
<212> TYPE: PRT
<213> ORGANISM: Artificial Sequence
<220> FEATURE:
<223> OTHER INFORMATION: A synthetic polypeptide

<400> SEQUENCE: 29

Ser Gly Phe Ala Arg Ala Pro Ala Asn Gly Thr Arg
1               5                   10

<210> SEQ ID NO 30
<211> LENGTH: 12
<212> TYPE: PRT
<213> ORGANISM: Artificial Sequence
<220> FEATURE:
<223> OTHER INFORMATION: A synthetic polypeptide

<400> SEQUENCE: 30

Ala Arg Ala Pro Ala Asn Gly Thr Arg Ser Ser Arg
1               5                   10

<210> SEQ ID NO 31
<211> LENGTH: 12
<212> TYPE: PRT
<213> ORGANISM: Artificial Sequence
<220> FEATURE:
<223> OTHER INFORMATION: A synthetic polypeptide

<400> SEQUENCE: 31

Pro Ala Asn Gly Thr Arg Ser Ser Arg Ser Gly Phe
1               5                   10

<210> SEQ ID NO 32
<211> LENGTH: 12
<212> TYPE: PRT
<213> ORGANISM: Artificial Sequence
<220> FEATURE:
<223> OTHER INFORMATION: A synthetic polypeptide

<400> SEQUENCE: 32

Gly Thr Arg Ser Ser Arg Ser Gly Phe Lys Val Trp
1               5                   10

<210> SEQ ID NO 33
<211> LENGTH: 12
<212> TYPE: PRT
<213> ORGANISM: Artificial Sequence
<220> FEATURE:
<223> OTHER INFORMATION: A synthetic polypeptide

<400> SEQUENCE: 33

```
Ser Ser Arg Ser Gly Phe Lys Val Trp Phe Arg Asp
1               5                   10
```

<210> SEQ ID NO 34
<211> LENGTH: 12
<212> TYPE: PRT
<213> ORGANISM: Artificial Sequence
<220> FEATURE:
<223> OTHER INFORMATION: A synthetic polypeptide

<400> SEQUENCE: 34

```
Ser Gly Phe Lys Val Trp Phe Arg Asp Pro Leu Glu
1               5                   10
```

<210> SEQ ID NO 35
<211> LENGTH: 12
<212> TYPE: PRT
<213> ORGANISM: Artificial Sequence
<220> FEATURE:
<223> OTHER INFORMATION: A synthetic polypeptide

<400> SEQUENCE: 35

```
Lys Val Trp Phe Arg Asp Pro Leu Glu Asp Asp Ala
1               5                   10
```

<210> SEQ ID NO 36
<211> LENGTH: 12
<212> TYPE: PRT
<213> ORGANISM: Artificial Sequence
<220> FEATURE:
<223> OTHER INFORMATION: A synthetic polypeptide

<400> SEQUENCE: 36

```
Phe Arg Asp Pro Leu Glu Asp Asp Ala Ala Pro Ala
1               5                   10
```

<210> SEQ ID NO 37
<211> LENGTH: 12
<212> TYPE: PRT
<213> ORGANISM: Artificial Sequence
<220> FEATURE:
<223> OTHER INFORMATION: A synthetic polypeptide

<400> SEQUENCE: 37

```
Pro Leu Glu Asp Asp Ala Ala Pro Ala Arg Thr Pro
1               5                   10
```

<210> SEQ ID NO 38
<211> LENGTH: 12
<212> TYPE: PRT
<213> ORGANISM: Artificial Sequence
<220> FEATURE:
<223> OTHER INFORMATION: A synthetic polypeptide

<400> SEQUENCE: 38

```
Asp Asp Ala Ala Pro Ala Arg Thr Pro Ala Ala Pro
1               5                   10
```

<210> SEQ ID NO 39
<211> LENGTH: 12
<212> TYPE: PRT
<213> ORGANISM: Artificial Sequence
<220> FEATURE:
<223> OTHER INFORMATION: A synthetic polypeptide

<400> SEQUENCE: 39

```
Ala Pro Ala Arg Thr Pro Ala Ala Pro Asp Tyr Thr
```

```
1               5               10
```

<210> SEQ ID NO 40
<211> LENGTH: 12
<212> TYPE: PRT
<213> ORGANISM: Artificial Sequence
<220> FEATURE:
<223> OTHER INFORMATION: A synthetic polypeptide

<400> SEQUENCE: 40

```
Arg Thr Pro Ala Ala Pro Asp Tyr Thr Val Val Ala
1               5                   10
```

<210> SEQ ID NO 41
<211> LENGTH: 12
<212> TYPE: PRT
<213> ORGANISM: Artificial Sequence
<220> FEATURE:
<223> OTHER INFORMATION: A synthetic polypeptide

<400> SEQUENCE: 41

```
Ala Ala Pro Asp Tyr Thr Val Val Ala Ala Arg Leu
1               5                   10
```

<210> SEQ ID NO 42
<211> LENGTH: 12
<212> TYPE: PRT
<213> ORGANISM: Artificial Sequence
<220> FEATURE:
<223> OTHER INFORMATION: A synthetic polypeptide

<400> SEQUENCE: 42

```
Asp Tyr Thr Val Val Ala Ala Arg Leu Lys Ser Ile
1               5                   10
```

<210> SEQ ID NO 43
<211> LENGTH: 12
<212> TYPE: PRT
<213> ORGANISM: Artificial Sequence
<220> FEATURE:
<223> OTHER INFORMATION: A synthetic polypeptide

<400> SEQUENCE: 43

```
Thr Val Val Ala Ala Arg Leu Lys Ser Ile Leu Arg
1               5                   10
```

<210> SEQ ID NO 44
<211> LENGTH: 9
<212> TYPE: PRT
<213> ORGANISM: Artificial Sequence
<220> FEATURE:
<223> OTHER INFORMATION: A synthetic polypeptide

<400> SEQUENCE: 44

```
Ser Asp Asp Asp Gly Pro Ala Ser Asn
1               5
```

<210> SEQ ID NO 45
<211> LENGTH: 10

```
<212> TYPE: PRT
<213> ORGANISM: Artificial Sequence
<220> FEATURE:
<223> OTHER INFORMATION: A synthetic polypeptide

<400> SEQUENCE: 45

Glu Ser Asp Asp Asp Gly Pro Ala Ser Asn
1               5                   10
```

BOVINE HERPESVIRUS DETECTION AND TREATMENT

SEQUENCE LISTING

The instant application contains a Sequence Listing which has been submitted electronically in ASCII format and is hereby incorporated by reference in its entirety. Said ASCII copy, created on Jun. 23, 2018, is named Sequence_Listing_15501094.txt and is 12,288 bytes in size.

This application is a Continuation of U.S. patent application Ser. No. 15/501,094, filed on Feb. 1, 2017, which is a National Stage Entry of International Application PCT/US2015/043112, filed on Jul. 31, 2015, which claims benefit of the filing date of U.S. Provisional Patent Application No. 62/032,098, filed Aug. 1, 2014, the contents of each of which are specifically incorporated herein.

BACKGROUND

Bovine herpesvirus type 1 (BoHV-1) is a viral pathogen of cattle that can cause severe respiratory tract infections known as infectious bovine rhinotracheitis (IBR), abortion in pregnant cows. BoHV-1 is also a significant contributor to the development of Bovine respiratory disease complex (BRDC). BRDC is a multifactoral disease in cattle involving initial viral respiratory infection that may include BoHV-1, bovine respiratory syncytial virus (BRSV) and bovine viral diarrheal virus (BVDV) followed by secondary bacterial infection and severe bronchopneumonia. BRDC costs the US cattle industry alone more than $1 billion annually. The ability of BoHV-1 to immunosuppress infected cattle, to establish a lifelong latent infection in the trigeminal ganglia (TG) of infected animals, to reactivate from latency upon stress, and to be transported anterogradely from neuron cell bodies in the trigeminal ganglia to axon termini in the nasal and upper respiratory epithelium followed by replication in the upper respiratory tract predisposes the latently infected animals to BRDC. Therefore, BoHV-1 is considered to be an important initiator of BRDC.

Currently, the only vaccine allowed in EU countries against BoHV-1 is the entire gE-deleted BoHV-1 vaccine. By using the gE gene-deleted marker vaccine, BoHV-1 has largely been eradicated in a number of European countries. The gE-deleted vaccine vaccinated cattle can be differentiated from the wild type (wt) BoHV-1-infected cattle by various assays and, in the field, the gE-deleted BoHV-1 vaccine is being used in conjunction with a serological marker test marketed by IDEXX. Because the gE-deleted BoHV-1 vaccine is distinguishable from wild type BoHV-1, it is a "Differentiating Infected from Vaccinated Animals" (DIVA) vaccine. DIVA status for any BoHV-1 vaccine is important for the enforcement of BoHV-1 eradication program, and is necessary for marketing a BoHV-1 vaccine in Europe. As a result, the gE-deleted BoHV-1 vaccine is the only BoHV-1 vaccine marketed in Europe.

The inventors have developed a new BoHV-1 vaccine called the BoHV-1 tmv vaccine. Comparative tests indicate that the vaccine efficacy the BoHV-1 tmv is significantly better than the gE-deleted BoHV-1 vaccine. Tests also indicate that the IDEEX test that is currently used to distinguish gE-deleted vaccine vaccinated cattle from wild type (wt) BoHV-1-infected cattle is not suitable for distinguishing the BoHV-1 tmv-vaccinated calves from BoHV-1 wt-infected calves. This may be because BoHV-1tmv has a carboxy-terminal deletion of amino acids 452-575 but it retains approximately two-thirds of the gE coding region. Hence, amino acids 1-451 of gE, including the extracellular and transmembrane domains, are present in the inventors' BoHV-1 tmv vaccine. Therefore, a serological marker test that would distinguish the BoHV-1tmv vaccinated animals from the BoHV-1 wt infected animals is necessary before the improved BoHV-1 tmv vaccine can be introduced in the field.

SUMMARY

Described herein is an assay for detection of a highly efficacious recombinant BoHV-1 triple mutant virus (BoHV-1 tmv). Compared to wild type BoHV-1, the BoHV-1 triple mutant virus lacks the immunosuppressive functions encoded within UL49.5 (i.e., the BoHV-1 tmv vaccine does not have UL49.5 amino acids 30-32 and 80-96). In addition, the BoHV-1 tmv vaccine lacks the gE cytoplasmic tail (gE CT residues 451-575), which is associated with virulence function. In addition, the BoHV-1 tmv vaccine lacks the entire 435 base pair long Us9 open reading frame. Results show that viruses with deletions of the gE cytoplasmic tail and the Us9 open reading frame do not reactivate from latency in the trigeminal ganglia because they cannot be transported anterogradely. Therefore, the BoHV-1 tmv strain may not shed within bovine nasal secretions following latency reactivation. Because of these and other properties, the vaccine efficacy the BoHV-1 tmv is significantly better than the BoHV-1 gE-deleted virus, and comparative tests demonstrate that this is the case. For example, the protective efficacy of the BoHV-1 tmv vaccine against challenge by wild type BoHV-1 is significantly better than observed for the gE-deleted vaccine virus.

One aspect of the invention is a method comprising: (a) contacting a test sample with at least one polypeptide or peptide to form an assay mixture, where the at least one polypeptide or peptide has or includes a sequence with at least 95% sequence identity to any of SEQ ID NO:1, 4-44, or 45; and (b) detecting or measuring whether a complex between the at least one polypeptide or peptide and antibodies is present in the assay mixture.

Another aspect of the invention is a device comprising a solid surface and at least one polypeptide or peptide that has a sequence with at least 95% sequence identity to any of SEQ ID NO:1, 4-44, or 45. Another aspect is a device comprising a solid surface and an antibody that selectively binds at least one polypeptide or peptide antigen with a sequence selected from SEQ ID NO:1, 4-44, or 45.

Another aspect of the invention is an expression cassette or expression vector that includes a nucleic acid segment encoding a polypeptide or peptide comprising a sequence with at least 95% sequence identity to any of SEQ ID NO:1, 4-44, or 45. Another aspect is an expression cassette or expression vector comprising a nucleic acid segment that includes a sequence with at least 95% sequence identity to SEQ ID NO:2 or 3.

Another aspect is a device that includes a solid surface and at least one polypeptide or peptide comprising or consisting essentially of a sequence with at least 95% sequence identity to any of SEQ ID NO:1, 4-44, or 45. Another aspect is a kit that includes such a device, and instructions for using the device.

Another aspect of the invention is a kit that includes instructions for use of the kit components, and any of the following separately packaged components: (a) at least one polypeptide or peptide comprising or consisting essentially of a sequence with at least 95% sequence identity to any of SEQ ID NO:1, 4-44, or 45; (b) a binding entity that specifically binds to at least one polypeptide or peptide comprising or consisting essentially of a sequence with at least 95% sequence identity to any of SEQ ID NO:1, 4-44, or 45; (c) a secondary binding entity that specifically binds to at least one polypeptide or peptide comprising or consisting essentially of a sequence with at least 95% sequence identity to any of SEQ ID NO:1, 4-44, or 45; (d) a label or a reagent for developing a signal from a label; or (e) any combination thereof.

DESCRIPTION OF THE FIGURES

FIG. 1A-1F show the design and expression strategy for generating a recombinant gE cytoplasmic tail (CT) polypeptide fragment based upon the predicted BoHV-1 gE CT amino acid sequence. FIG. 1A is a schematic diagram the BHV-1 envelope protein, gE, showing the extracellular (Ecto), transmembrane (TM) and cytoplasmic tail (CT) domains. FIG. 1B is the predicted amino acid sequence of BoHV-1 gE CT domain (BoHV-1 gE residues 451-570; SEQ ID NO:1). FIG. 1C is the nucleotide sequence of the BoHV-1 gE CT coding region, which was codon optimized for *E. coli* expression (SEQ ID NO:2). FIG. 1D is the nucleotide sequence of the BoHV-1gE CT coding region fused at the 3' end with a segment encoding six histidine residues (SEQ ID NO:3). This construct was placed in the pET-43.1a vector. FIG. 1E is the amino acid sequence (SEQ ID NO:4) of the BoHV-1 gE CT-His antigen expressed in *E. coli* from the pET-43.1a gE CT-His expression vector. The estimated isoelectric point (pI) and molecular weight (MW) of the recombinant BoHV-1 gE CT-His antigen is also shown. FIG. 1F is a schematic diagram of BoHV-1 $U_L$49.5 Δ30-32 CT-null/gE-CTΔ/Us9Δ virus genome (BoHV-1 tiny) showing (1) a schematic of the BoHV-1 genome with the locations of $U_L$49.5 (gN), gE, Us9 and bICP22 open reading frames; (2) a schematic of the BoHV-1 $U_L$49.5 Δ30-32 CT-null genome; and (3) a schematic of pBoHV-1 gE-CTΔ/Us9Δ plasmid showing the location and sizes of deleted sequences (gE CT, Us9 and Us9-bICP22 intergenic region), the flanking upstream gE (ectodomain and transmembrane) and downstream bICP22 sequences.

FIG. 2A-2D show SDS-PAGE separated immunoblots used to analyze the recombinant BoHV-1 gE-CT His polypeptide (SEQ ID NO:4) and the anti-BoHV-1 gE CT-specific monoclonal antibody MAb 2H8F3 generated as described herein.

FIG. 2A shows a Coomassie blue stained 12% SDS-PAGE gel containing the electrophoretically purified gE CT-His (SEQ ID NO:1) polypeptide (lane 1) and the immunoblotting results of the same gE CT-His protein-containing lane after reaction with an anti-His antibody (lane 2). FIG. 2B shows a Coomassie blue-stained 12% SDS-PAGE gel containing gE CT-His polypeptide electrophoretically separated under reducing (lane 1) and non-reducing (lane 2) conditions. Molecular weight markers are shown in lane (M). FIG. 2C shows an immunoblot with the purified gE CT-His (SEQ ID NO:1) polypeptide in both lanes (1) and (2) after reaction with fluorescently labeled BoHV-1 gE CT-specific MAb2H8F3 antibodies. FIG. 2D shows an immunoblot of the purified gE CT-His (SEQ ID NO:1) polypeptide in both lanes (1) and (2) after reaction with fluorescently labeled anti-GST antibodies.

FIG. 3 shows a MALD1-TOF Mass Spectrometry plot of gE CT-His protein.

FIG. 4A-4B illustrates immunoblotting analysis of the MAb 2HF83 to show its reactivity against BoHV-1 wt and BoHV-1 tmv-infected cell lysates. FIG. 4A shows an immunoblot of mock-, BoHV-1 wt- and BoHV-1 tmv-infected MDBK cell lysates separated in a 10% SDS-PAGE after reaction with the gE Ct-specific MAb 2HF83. FIG. 4B shows an immunoblotting analysis of an identical Western blot with a gE ectodomain-specific rabbit polyclonal antibody. Note that an approximate 68 kD gE CT-specific band is not recognized by the MAb 2HF83 in FIG. 4A but is recognized by the gE ectodomain-specific rabbit polyclonal antibody in FIG. 4B.

FIG. 5 graphically illustrates ELISA epitope mapping results. The absorbance at 450 nm observed for reaction of the HRP conjugated MAb2H8F3 antibody for each peptide library sample is shown. Peptides with numbers 1-39 (SEQ ID NOs:5-43) are 12-mers with separate sequences from the *E. coli* expressed recombinant gE CT-His polypeptide. Peptide well No. 40 contains streptavidin as a blank control. Peptide well No. 41 contains purified *E. coli* expressed recombinant gE CT-His protein, which was used for the production of the MAb2H8F3 antibody. As shown, the MAb2H8F3 antibody was bound to peptide Nos. 16 and 17 (SEQ ID NOs: 20 and 21).

FIG. 6 is a schematic diagram of the pET-43.1a(+) expression vector

FIG. 7A-7F are schematic drawings of devices that can be employed for detecting and monitoring BoHV-1 infection (and for identifying animals that would benefit from vaccination with the BoHV-1 tmv vaccine). FIG. 7A is a schematic drawing of a lateral flow BoHV-1 detection device. FIG. 7B is a schematic drawing of a lateral flow BoHV-1 detection device illustrating display of a signal (***) after testing a bodily fluid sample. FIG. 7C is a schematic drawing of a device with two electrical conducting nanowires, for example, an electrical direct-charge transfer conductometric biosensor. FIG. 7D is a schematic drawing of the device shown in FIG. 1C illustrating direct charge transfer (*) between two electrical conducting nanowires after testing a bodily fluid sample. FIG. 7E is a schematic drawing of a device with a longer and a shorter nanowire. FIG. 7F is a schematic drawing of a device a longer and a shorter nanowire illustrating that a signal (***) can be transmitted along a nanowire to a transmitter after testing a bodily fluid.

FIG. 8 illustrates a device and a method of using a test strip for performing an assay to detect BoHV-1 infection and/or animals that would benefit from vaccination with the BoHV-1 tmv vaccine.

DETAILED DESCRIPTION

Methods and compositions for detecting and distinguishing BoHV-1 infected animals from vaccinated and/or non-infected animals are described herein.

Bovine Herpesvirus Type 1 (BoHV-1)

Bovine herpesvirus type 1 (BHV-1) is a pathogen of cattle that can cause severe respiratory tract infection known as infectious bovine rhinotracheitis (IBR), which can cause abortion in pregnant cows (Kaashoek et al., Vet Rec 139 (17):416-21 (1996); Tikoo et al., Adv Virus Res 45:191-223 (1995); Jones & Chowdhury, Animal Health Res Rev 8(2): 187-205 (2007); U.S. Pat. No. 6,221,360). BoHV-1 is also an important component of the Bovine Respiratory Disease Complex (BRDC or "Shipping fever"). During primary infection, BoHV-1 replicates in the nasal and upper respiratory tract epithelium and transiently depresses cell-mediated immunity and evades the host cytotoxic $CD8^+$ T cell recognition by down regulating the cell surface expression of major histocompatibility complex class I (MHC-I) molecules. This immunosuppression combined with lesions in

Figure 1A:
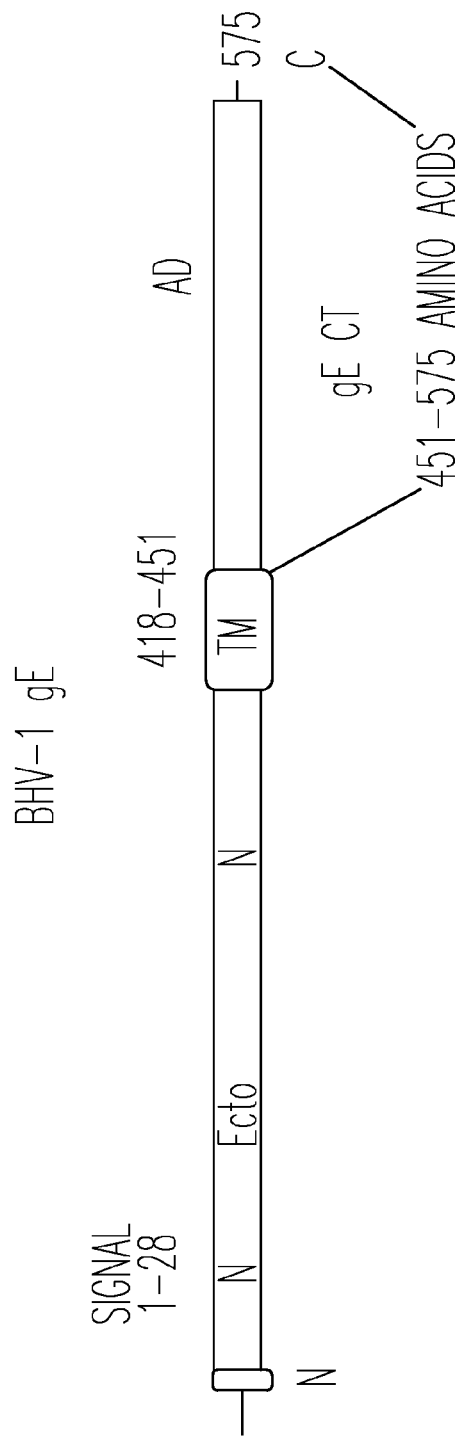

the upper respiratory tract facilitates secondary bacterial infections and pneumonia. Both IBR disease and BRDC cause considerable losses for the cattle industry worldwide and cost the US cattle industry at least $1 billion dollars annually (Tikoo et al., Adv Virus Res 45:191-223 (1995)).

Another problem with BoHV-1 infection in cattle is that the virus establishes a life-long latency in trigeminal ganglia following the primary infection (Jones & Chowdhury, Animal Health Res Rev 8(2):187-205 (2007)). During the primary infection, the virus enters the sensory nerve endings (axon terminals) of the trigeminal nerve in the nasopharynx and is transported up the axon retrogradely to the neuronal cell bodies in the trigeminal ganglia where BoHV-1 establishes life-long latency (id.). Periodically throughout the life of the animal, the latent virus in the trigeminal ganglia reactivates due to immunosuppression or stress. Following reactivation, the virus is transported down the axon to the primary infection sites in the nose and/or eye. The viral infection causes ocular and nasal virus shedding (id.), which facilitates virus transmission to other cattle. Thus this reactivation followed by shedding maintains an ongoing viral infection in susceptible cattle populations.

In BoHV-1-infected cells, envelope protein $U_L49.5$ (a BoHV-1 homolog of envelope glycoprotein N (gN)) was found to block the Transporter associated with antigen presentation (TAP) function required for the display of viral peptides on the cell surface. To promote the immune response from the host, the MHC-I molecules must be loaded with viral peptides. However, BoHV-1 $U_L49.5$ binds to the TAP complex, blocks TAP conformational changes, and degrades the TAP (Lipinska et al., J Virol 80(12):5822-32 (2006)). Consequently, peptides are not loaded onto the MHC-I molecules in the endoplasmic reticulum, which is required for the MHC-I transport to cell surface and cell surface expression. This results in transient MHC-I downregulation in a susceptible host and helps the virus evade destruction by the CD8+ T cells at an early stage of virus infection of the host.

BoHV-1 mutants have been made and analyzed for use as vaccines. One commercially available vaccine is based on a deletion of the complete glycoprotein E (gE) gene. Following intranasal infection, both the gE-deleted (the entire gE gene deleted) and the inventors' gE cytoplasmic tail (CT)-truncated BHV-1 recombinant viruses were determined to be equally attenuated in calves and to have defective anterograde axonal transport (Liu et al., J Virol 82(15):7432-42 (2008); Chowdhury et al., J. Neurovirol. 17:457-465 (2010)). Therefore, following dexamethasone-induced reactivation in the trigeminal ganglia, no nasal virus shedding in calves infected with either recombinant virus was seen (Liu et al., J Virol 82(15):7432-42 (2008)). Importantly, BHV-1 gE cytoplasmic tail-deleted virus-infected calves have two-fold higher serum neutralizing titers relative to calves infected with the entire gE-deleted virus (id.).

BoHV-1 gE

The BoHH-1 genome consists of a linear double-stranded DNA molecule of about 135.3 kb that encodes for approximately 70 proteins. Twelve of these proteins (gB, gC, gD, gE, gG, gI, gH, gK, gL, gM, UL49.5 and Us9) are envelope proteins, and the gB, gC, gD, gE, gG, gI, gH, gK, gL, gM, protein are glycosylated envelope proteins. Envelope glycoproteins gE and gI form complexes and gE is involved in viral intercellular spread (cell-to-cell spread). The BoHV-1 gE open reading frame (ORF) is predicted to contain 575 amino acid (aa) residues with a 28 amino acid cleavable signal sequence. The structure of glycoprotein E (gE) corresponds to a type I transmembrane glycoprotein. The gE glycoprotein contains three distinct domains: a 387 amino acid long hydrophilic extracellular domain (ecto-domain), a 33 amino acid long hydrophobic transmembrane domain, and a 125 amino acid long highly charged cytoplasmic domain/tegument domain. The mature gE is phosphorylated and glycosylated with an apparent molecular mass of about 92 kD.

Figure 1F:
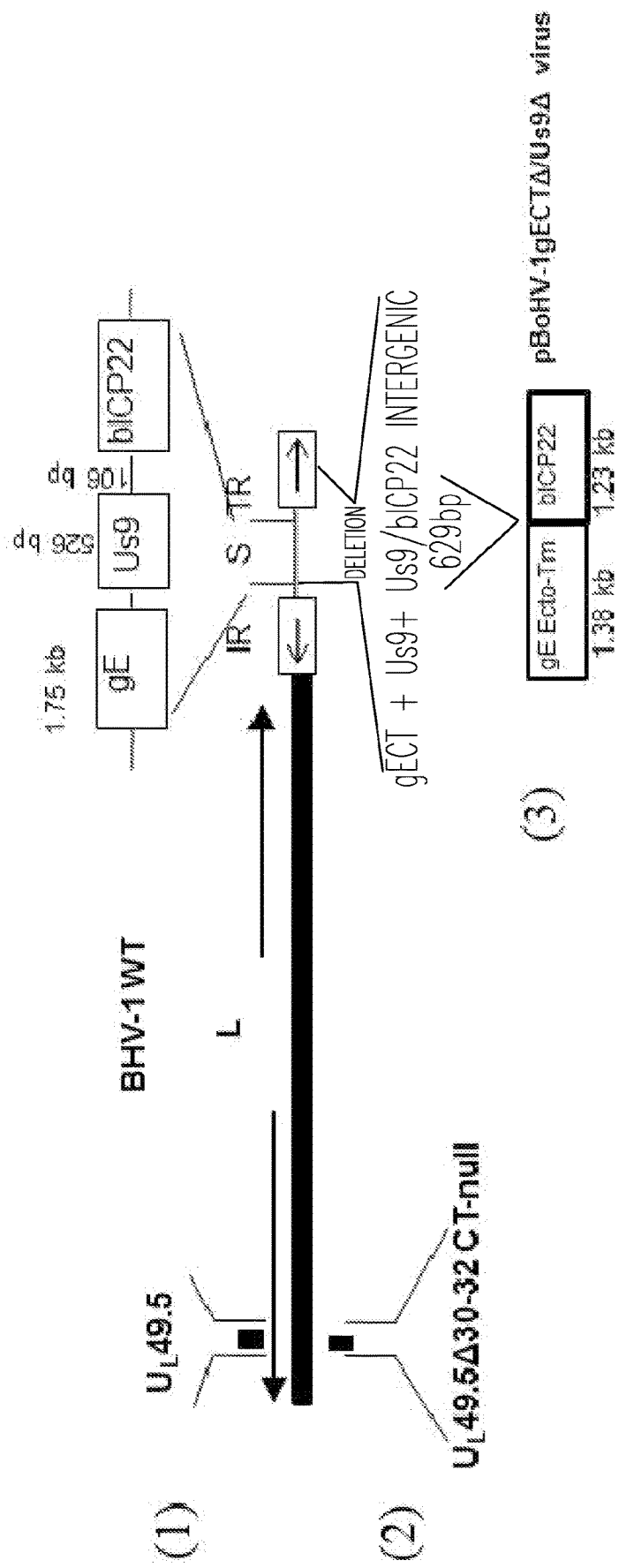

The BoHV-1 tmv vaccine previously generated by the inventors is a recombinant BoHV-1 triple mutant virus that lacks the immunosuppressive (deletion of UL49.5 residues 30-32 and 80-96), the virulence (deletion of the gE cytoplasmic tail residues 452-575), and the anterograde neuronal transport (deletion of gE cytoplasmic tail and the entire 435 bp long Us9 ORF) properties (Chowdhury et al., *Vaccine* 32(39):4909-4915 (2014)) (see, FIG. 1F). Although the inventors' BoHV-1 tmv vaccine is missing a C-terminal part of the glycoprotein E cytoplasmic tail, it retains and expresses the N-terminal 1-451 amino acids of gE, including the extracellular and transmembrane domains of the BoHV-1 glycoprotein E.

The compositions, methods, kits and devices described herein are useful for distinguishing animals that are vaccinated with the BoHV-1 tmv vaccine from those that are infected with BoHV-1. In addition, the compositions, methods, kits and devices described herein are also useful for distinguishing animals that not infected with BoHV-1 from those that are infected. Such compositions, methods, kits and devices can detect antibodies and/or antigens that are present in BoHV-1-infected animals but they do not detect any such antibodies or antigens in non-infected animals or in animals that are vaccinated with the BoHV-1 tmv vaccine.

In particular, the compositions, methods, kits and devices described herein detect a portion of glycoprotein E that is not part of the BoHV-1 tmv vaccine—the glycoprotein E cytoplasmic tail. The structure of glycoprotein E is schematically shown in FIG. 1A. The part of glycoprotein E that is missing in the BoHV-1 tmv vaccine is the 451-575 amino acid glycoprotein E cytoplasmic tail (gE CT), with the sequence shown below (SEQ ID NO:1; FIG. 1B).

```
  1 ASQKRTYDIL NPFGPVYTSL PTNEPLDVVV PVSDDEFSLD

41 EDSFADDDSD DDGPASNPPA DAYDLAGAPE PTSGFARAPA

81 NGTRSSRSGF KVWFRDPLED DAAPARTPAA PDYTVVAARL

121 KSILR
```

This missing cytoplasmic tail domain of the BoHV-1 gE protein is useful as an antigen for developing assays that detect BoHV-1 infection, thereby identifying infected animals. Non-infected animals and animals that have been vaccinated with the BoHV-1 tmv vaccine do not develop antibodies against the cytoplasmic tail domain of the BoHV-1 gE protein and are not detected with the gE CT antigen-based assays described herein.

A nucleic acid that encodes the SEQ ID NO:1 glycoprotein E cytoplasmic tail is shown below (SEQ ID NO:2; FIG. 1C).

```
  1 GCATCGCAAA AGCGTACCTA TGATATTCTG AACCCGTTTG

41 GTCCGGTCTA CACGAGCCTG CCGACGAACG AACCGCTGGA

61 TGTTGTTGTG CCTGTTAGTG ATGACGAATT TTCCCTGGAT

121 GAAGACTCAT TCGCCGATGA CGATTCGGAC GATGACGGTC
```

```
161 CGGCAAGCAA CCCGCCGGCA GATGCTTATG ATCTGGCAGG

201 TGCACCGGAA CCGACCTCTG GTTTTGCACG TGCTCCGGCG

241 AATGGCACGC GTAGCTCTCG CTCCGGTTTT AAAGTCTGGT

281 TCCGCGATCC GCTGGAAGAT GACGCGGCCC CGGCGCGTAC

321 CCCGGCGGCA CCGGACTACA CCGTGGTTGC GGCCCGTCTG

361 AAGAGCATCC TGCGT
```

A variant BoHV-1 cytoplasmic tail domain with an N-terminal methionine and an N-terminal six histidine tag is also useful an antigen and is readily detectable/isolatable due to the presence of the histidine tag. The sequence of this polypeptide is shown below (SEQ ID NO:4; FIG. 1E).

```
  1 MHHHHHHASQ KRTYDILNPF GPVYTSLPTN EPLDVVVPVS

41 DDEFSLDEDS FADDDSDDDG PASNPPADAY DLAGAPEPTS

81 GFARAPANGT RSSRSGFKVW FRDPLEDDAA PARTPAAPDY

121 TVVAARLKSI LR
```

An *E. coli* codon-optimized nucleic acid sequence that encodes the SEQ ID NO:4 polypeptide is shown below (SEQ ID NO:3; FIG. 1D).

```
  1 CATATGCATC ACCACCATCA CCACGCATCG CAAAAGCGTA

41 CCTATGATAT TCTGAACCCG TTTGGTCCGG TCTACACGAG

81 CCTGCCGACG AACGAACCGC TGGATGTTGT TGTGCCTGTT

121 AGTGATGACG AATTTTCCCT GGATGAAGAC TCATTCGCCG

161 ATGACGATTC GGACGATGAC GGTCCGGCAA GCAACCCGCC

201 GGCAGATGCT TATGATCTGG CAGGTGCACC GGAACCGACC

241 TCTGGTTTTG CACGTGCTCC GGCGAATGGC ACGCGTAGCT

281 CTCGCTCCGG TTTTAAAGTC TGGTTCCGCG ATCCGCTGGA

321 AGATGACGCG GCCCCGGCGC GTACCCCGGC GGCACCGGAC

361 TACACCGTGG TTGCGGCCCG TCTGAAGAGC ATCCTGCGTT

401 AATGACTCGA G
```

The sequences of the polypeptides, peptides, and nucleic acids described herein can vary somewhat from the sequences recited herein for the wild type BoHV-1 virion. In addition, the sequences of the polypeptides, peptides, and nucleic acids employed in the methods, compositions, devices, and kits described herein can also vary. For example, the nucleic acids encoding the polypeptides and peptides described herein can be codon-optimized for expression in a variety of host cells (e.g., in various prokaryotic or eukaryotic host cell species or strains). Hence, the polypeptides, peptides, and nucleic acids employed and/or detected herein can have at least 75% sequence identity, or at least 80% sequence identity, or at least 85% sequence identity, or at least 90%, or at least 95% sequence identity to any of SEQ ID NO:1-45.

Sequence identity and sequence variation can be evaluated using sequence analysis software (e.g., via the NCB' tools, or the Sequence Analysis Software Package of the Genetics Computer Group, University of Wisconsin Biotechnology Center, 1710 University Avenue. Madison, Wis. 53705). Software can be employed to match similar sequences by assigning degrees of sequence identity to various substitutions, deletions, insertions, and other modifications. Conservative amino acid substitutions, for example, typically include substitutions within the following groups: the group of glycine, alanine; valine, isoleucine, and leucine; the group of aspartic acid, glutamic acid, asparagine, and glutamine; the group of serine and threonine; the group of lysine and arginine; and the group of phenylalanine and tyrosine.

Expression Cassettes or Vectors

The nucleic acids with sequences that are at least 95% identical to SEQ ID NO:2 or 3 are useful for efficiently expressing the glycoprotein E cytoplasmic tail, which can be used as antigen (or to generate antibodies) for detecting BoHV-1 infection and distinguishing animals that have been vaccinated with the BoHV-1 tmv vaccine from those that need to be vaccinated.

Antigenic peptide fragments of the glycoprotein E cytoplasmic tail are also useful as antigens for detection of BoHV-1 infection, and for generating antibodies for detection of BoHV-1 and BoHV-1 infection. Examples of such antigenic fragments of the BoHV-1 glycoprotein E cytoplasmic tail include polypeptides and/or peptides with a sequence that is at least 95% identical to any of SEQ ID NOs: 1, 4, 5-44 or 45. These polypeptides and/or peptides can be encoded within expression cassettes or expression vectors that include one or more nucleic acid segments.

For example, one of skill in the art can prepare an expression cassette or expression vector that can express one or more encoded BoHV-1 glycoprotein E cytoplasmic tail polypeptides or peptides. Host cells can be transformed by the expression cassette or expression vector, and the expressed polypeptides or peptides can be isolated therefrom. Some procedures for making such genetically modified host cells are described below.

Promoters: Nucleic acids or nucleic acid segments encoding the BoHV-1 glycoprotein E cytoplasmic tail can be operably linked to a promoter, which provides for expression of an mRNA encoding the BoHV-1 glycoprotein E cytoplasmic tail polypeptides or peptides. The promoter can be a promoter functional in a host cell such as a viral promoter, a bacterial promoter or a mammalian promoter. The promoter can be a heterologous promoter. As used herein, "heterologous" when used in reference to a gene or nucleic acid refers to a gene or nucleic acid that has been manipulated in some way. For example, a heterologous promoter is a promoter that contains sequences that are not naturally linked to an associated coding region. Thus, a heterologous promoter is not the same as the natural BoHV-1 promoter that drives expression of glycoprotein E.

A BoHV-1 glycoprotein E cytoplasmic tail nucleic acids are operably linked to the promoter when so that the BoHV-1 glycoprotein E cytoplasmic tail coding region is located downstream from the promoter. The operable combination of the promoter with the BoHV-1 glycoprotein E cytoplasmic tail coding region is a key part of the expression cassette or expression vector.

Promoter regions are typically found in the flanking DNA upstream from the coding sequence in both prokaryotic and eukaryotic cells. A promoter sequence provides for regulation of transcription of the downstream gene sequence and typically includes from about 50 to about 2,000 nucleotide base pairs. Promoter sequences also contain regulatory sequences such as enhancer sequences that can influence the level of gene expression. Some isolated promoter sequences can provide for gene expression of heterologous DNAs, that is a DNA different from the native or homologous DNA.

Promoter sequences are also known to be strong or weak, or inducible. A strong promoter provides for a high level of gene expression, whereas a weak promoter provides a very low level of gene expression. An inducible promoter is a promoter that provides for the turning on and off of gene expression in response to an exogenously added agent, or to an environmental or developmental stimulus. For example, a bacterial promoter such as the $P_{tac}$ promoter can be induced to vary levels of gene expression depending on the level of isothiopropylgalactoside added to the transformed cells. Promoters can also provide for tissue specific or developmental regulation. An isolated promoter sequence that is a strong promoter for heterologous DNAs is advantageous because it provides for a sufficient level of gene expression for easy detection and selection of transformed cells and provides for a high level of gene expression when desired. In some embodiments, the promoter is an inducible promoter and/or a tissue-specific promoter.

Examples of promoters that can be used include, but are not limited to, the T7 promoter (e.g., optionally with the lac operator), the CaMV 35S promoter (Odell et al., Nature. 313:810-812 (1985)), the CaMV 19S promoter (Lawton et al., Plant Molecular Biology. 9:315-324 (1987)), nos promoter (Ebert et al., Proc. Natl. Acad. Sci. USA. 84:5745-5749 (1987)), Adh1 promoter (Walker et al., Proc. Natl. Acad. Sci. USA. 84:6624-6628 (1987)), sucrose synthase promoter (Yang et al., Proc. Natl. Acad. Sci. USA. 87:4144-4148 (1990)), α-tubulin promoter, ubiquitin promoter, actin promoter (Wang et al., Mol. Cell. Biol. 12:3399 (1992)), cab (Sullivan et al., Mol. Gen. Genet. 215:431 (1989)), PEPCase promoter (Hudspeth et al., Plant Molecular Biology. 12:579-589 (1989)), the CCR promoter (cinnamoyl CoA:NADP oxidoreductase, EC 1.2.1.44) isolated from Lolliuni perenne, (or a perennial ryegrass) and/or those associated with the R gene complex (Chandler et al., The Plant Cell. 1:1175-1183 (1989)).

Other constitutive or inducible promoters can be used with or without associated enhancer elements. Examples include a baculovirus derived promoter, the p10 promoter. Plant or yeast promoters can also be used.

Alternatively, novel tissue specific promoter sequences may be employed in the practice of the present invention. Coding regions from a particular cell type or tissue can be identified and the expression control elements of those coding regions can be identified using techniques available to those of skill in the art.

The nucleic acid encoding the BoHV-1 glycoprotein E cytoplasmic tail or peptide therefrom can be combined with the promoter by available methods to yield an expression cassette, for example, as described in Sambrook et al. (Molecular Cloning: A Laboratory Manual. Second Edition (Cold Spring Harbor, N.Y.: Cold Spring Harbor Press (1989); Molecular Cloning: A Laboratory Manual. Third Edition (Cold Spring Harbor, N.Y.: Cold Spring Harbor Press (2000)). For example, a plasmid containing a promoter such as the T7-lac promoter can be constructed or obtained from Snap Gene (see, e.g., website at snapgene.com/resources/plasmid_files/pct_and_duct_vectors_%28novagen%29/pET-43.1a %28+%29/). These and other plasmids are constructed to have multiple cloning sites having specificity for different restriction enzymes downstream from the promoter. The nucleic acid encoding the BoHV-1 glycoprotein E cytoplasmic tail or peptide therefrom can be subcloned downstream from the promoter using restriction enzymes and positioned to ensure that the DNA is inserted in proper orientation with respect to the promoter so that the DNA can be expressed as sense RNA.

Expression cassettes that include a promoter operably linked to a BoHV-1 glycoprotein E cytoplasmic tail polypeptide or peptide coding region can include other elements such as a segment encoding 3' nontranslated regulatory sequences, and restriction sites for insertion, removal and manipulation of segments of the expression cassettes. The 3' nontranslated regulatory DNA sequences can act as a signal to terminate transcription and allow for the polyadenylation of the resultant mRNA. The 3' nontranslated regulatory DNA sequence preferably includes from about 300 to 1,000 nucleotide base pairs and contains prokaryotic or eukaryotic transcriptional and translational termination sequences. Various 3' elements that are available to those of skill in the art can be employed. These 3' nontranslated regulatory sequences can be obtained as described in An (Methods in Enzymology. 153:292 (1987)). Many such 3' nontranslated regulatory sequences are already present in plasmids available from commercial sources such as Clontech, Palo Alto, Calif. The 3' nontranslated regulatory sequences can be operably linked to the 3' terminus of a BoHV-1 glycoprotein E cytoplasmic tail polypeptide or peptide coding region by available methods.

Once the nucleic acid encoding the BoHV-1 glycoprotein E cytoplasmic tail or peptide therefrom is operably linked to a promoter (e.g., and other selected elements), the expression cassette so formed can be subcloned into a plasmid or other vector (e.g., an expression vector). Such expression vectors can have a prokaryotic or eukaryotic replication origin, for example, to facilitate episomal replication in bacterial, vertebrate and/or yeast cells.

Examples of vectors that provide for easy selection, amplification, and transformation of the expression cassette in prokaryotic and eukaryotic cells include pET-43.1a(+), pUC-derived vectors such as pUC8, pUC9, pUC18, pUC19, pUC23, pUC119, and pUC120, pSK-derived vectors, pGEM-derived vectors, pSP-derived vectors, or pBS-derived vectors. The additional DNA sequences include origins of replication to provide for autonomous replication of the vector, additional selectable marker genes, such as antibiotic or herbicide resistance, unique multiple cloning sites providing for multiple sites to insert DNA sequences, and/or sequences that enhance transformation of prokaryotic and eukaryotic cells.

In order to improve identification of transformed cells, a selectable or screenable marker gene can be employed in the expression cassette or expression vector. "Marker genes" are genes that impart a distinct phenotype to cells expressing the marker gene and thus allow such transformed cells to be distinguished from cells that do not have the marker. Such genes may encode either a selectable or screenable marker, depending on whether the marker confers a trait which one can 'select' for by chemical means, i.e., through the use of a selective agent (e.g., an antibiotic), or whether it is simply a trait that one can identify through observation or testing, i.e., by 'screening' (e.g., the R-locus trait). Of course, many examples of suitable marker genes are known to the art and can be employed in the practice of the invention.

Included within the terms selectable or screenable "marker" genes are genes which encode a "secretable marker" whose secretion can be detected as a means of identifying or selecting for transformed cells. Examples include markers which encode a secretable antigen that can be identified by antibody interaction, or secretable enzymes that can be detected by their catalytic activity. Secretable proteins fall into a number of classes, including small, diffusible proteins detectable, e.g., by ELISA; and proteins that are inserted or trapped in the cell wall (e.g., proteins that include a leader sequence such as that found in the expression unit of extensin or tobacco PR-S).

Possible selectable markers for use in connection with the present invention include, but are not limited to, an ampicillin gene, which codes for the ampicillin antibiotic. Other examples include a neo gene (Potrykus et al., *Mol. Gen. Genet.* 199:183-188 (1985)) which codes for kanamycin resistance and can be selected for using kanamycin, G418, and the like; a mutant acetolactate synthase gene (ALS) which confers resistance to imidazolinone, sulfonylurea or other ALS-inhibiting chemicals (European Patent Application 154,204 (1985)); a methotrexate-resistant DHFR gene (Thillet et al., *J. Biol. Chem.* 263:12500-12508 (1988)); a dalapon dehalogenase gene that confers resistance to the herbicide dalapon; a mutated anthranilate synthase gene that confers resistance to 5-methyl tryptophan; a β-galactosidase gene, which encodes an enzyme for which there are chromogenic substrates; a luciferase (lux) gene (Ow et al., Science. 234:856-859.1986), which allows for bioluminescence detection; or an acquorin gene (Prasher et al., *Biochem. Biophys. Res. Comm.* 126:1259-1268 (1985)), which may be employed in calcium-sensitive bioluminescence detection, or a green or yellow fluorescent protein gene (Niedz et al., *Plant Cell Reports.* 14:403 (1995).

The expression cassettes and/or expression vectors can be introduced into a recipient host cell to create a transformed cell by available methods. The frequency of occurrence of cells taking up exogenous (foreign) DNA can be low, and it is likely that not all recipient cells receiving DNA segments or sequences will result in a transformed cell wherein the DNA is stably integrated into the host cell chromosome and/or expressed. Some may show only initial and transient gene expression. However, cells from virtually any species can be stably transformed, and those cells can be utilized to generate antigenic polypeptides or peptides.

Transformation of the host cells with expression cassettes or expression vectors can be conducted by any one of a number of methods available to those of skill in the art. Examples are: transformation by direct DNA transfer into host cells by electroporation, direct DNA transfer into host cells by PEG precipitation, direct DNA transfer to plant cells by microprojectile bombardment, and calcium chloride/heat shock.

Methods such as microprojectile bombardment or electroporation can be carried out with "naked" DNA where the expression cassette may be simply carried on any *E. coli*-derived plasmid cloning vector. In the case of viral vectors, it is desirable that the system retain replication functions, but lack functions for disease induction.

Once the glycoprotein E cytoplasmic tail polypeptide or peptide expression cassette or vector has been constructed and introduced into a host cell, the host cells can be screened for the ability to express the encoded glycoprotein E cytoplasmic tail polypeptide or peptide by available methods. For example, when the glycoprotein E cytoplasmic tail polypeptide or peptide has a poly-histidine tag, and the His-tagged glycoprotein E cytoplasmic tail polypeptide or peptide can be detected or isolated by use of anti-His tag antibodies. In another example, glycoprotein E cytoplasmic tail polypeptides or peptides can be detected using antibodies that bind to the polypeptides or peptides (e.g., via western blot or ELISA). Nucleic acids encoding the glycoprotein E cytoplasmic tail polypeptide or peptide can be detected by Southern blot, or nucleic acid amplification using complementary probes and/or primers.

Immunological Assays

The immunological assays described herein can detect BoHV-1 infection by detecting BoHV-1 antigens or antibodies in test samples obtained from animals.

No particular limitation is imposed on the type of the immunological assay method of the present invention, so long as the method involves formation of an antigen-binding entity (e.g., antibody) reaction. However, the assay method preferably includes a step for the formation of a complex between a BoHV-1 cytoplasmic tail antigen (or a peptide antigen thereof), and at least one antibody or binding entity.

Antibodies and antigens in test samples can be detected by techniques available in the art, such as radioimmunoassay, enzyme-linked immunosorbant assay (ELISA), "sandwich" immunoassay, in situ immunoassays (e.g., using colloidal gold, enzyme or radioisotope labels), western blot, agglutination assay (e.g., gel agglutination assay, hemagglutination assay and etc.), complement fixation assay, immunofluorescence assay, sandwich ELISA, immunoturbidimetry (TIA or LTIA (latex turbidimetric immunoassay)), immunochromatography, and immunoelectrophoresis assay and the like.

Test samples for detecting BoHV-1 antigens or antibodies can include tissues or bodily fluids collected from an animal such as whole blood, blood fractions, serum, nasal secretions, mucus, saliva, urine, feces, lung fluids, lung tissues, and the like. The test sample can be partially purified, filtered, fractionated (e.g., a supernatant or precipitate), or unpurified. For example, one convenient test sample is whole blood or serum.

In some cases, assays can be used to detect antibodies against the BoHV-1 cytoplasmic tail (or a peptide thereof), where the antibodies are present in serum samples obtained from BoHV-1 infected animals.

For example, antibody binding can be detected by use of ELISA where antibodies that can be present in a test sample bind a glycoprotein E cytoplasmic tail polypeptide or peptide (e.g., any polypeptide or peptide with SEQ ID NOs: 1, 4-44, or 45). Such antibodies can detected in bodily fluids, including but are not limited to serum or plasma samples. A device can be used for detecting by ELISA, for example, where an antigen is immobilized on a solid surface such as a test strip, lateral flow device, chip, or microtiter plate. The antigen can be a glycoprotein E cytoplasmic tail polypeptide or peptide (e.g., any polypeptide or peptide with SEQ ID NOs: 1, 4-44, 45, or a combination thereof). When antibodies are present in the test sample, those antibodies react with the immobilized antigen, and block binding by a labeled marker indicator binding entity. The marker indicator binding entity is specific for the immobilized antigen (i.e., the BoHV-1 glycoprotein E cytoplasmic tail polypeptide or peptide thereof) and binds to the immobilized antigen.

As described in the Examples, a competitive ELISA was developed where test sera were incubated in glycoprotein E cytoplasmic tail-His (gE CT-His) antigen-coated wells. After washing off the unbound sera, the indicator marker antibody was added, the plates are incubated again to allow any binding that may occur between the gE CT-His antigen coating the wells and the indicator marker antibody. The wells are then washed and the signal from an HRP-indicator marker antibody is observed. Test sera containing antibodies against BoHV-1 (i.e., sera from BoHV-1 infected animals) have a lower HRP signal than sera without such antibodies (i.e., uninfected animals), because the antibodies that the infected animals produce are unlabeled and will block the later binding by the indicator marker antibody to the gE CT-His antigen.

Hence, one method of detecting BoHV-1 infection can include (a) incubating a test sample in a device that includes aBoHV-1 (e.g., gE CT) antigen immobilized to a solid surface; (b) removing unbound test sample; (c) contacting the antigen immobilized on the solid surface with a labeled marker indicator binding entity; (d) removing unbound labeled marker indicator binding entity; and (e) quantifying the amount of labeled marker indicator binding entity bound to the immobilized antigen. High levels of antibodies in a test sample leads to a lower signal from the labeled marker indicator binding entity because the antibodies in the test sample block binding to the antigen by the labeled marker indicator binding entities. Hence, a test sample that exhibits a strong signal indicates that the animal from which the sample was obtained is not infected with BoHV-1. Such animals can be vaccinated with the BoHV-1 tmv vaccine, if they have not already been so vaccinated.

Another method of detecting BoHV-1 infection can include (a) incubating a test sample in a device that includes aBoHV-1 (e.g., gE CT) antigen; and (b) observing whether a signal is detectable, where the signal indicates that a complex has formed between the antigen and antibodies in the test sample. The method can optionally include quantifying the amount of signal.

The amount of labeled marker indicator binding entity bound to the antigen can be quantified by obtaining a quantified signal from the label bound to the marker indicator binding entity bound. For example, when the marker indicator binding entity is attached to a colored label or to a label that can give rise to a visually detectable signal, the signal can be quantified by measuring the amount of light transmitted or emitted (e.g., fluorescence or luminescence), or the amount of light absorbed. The Examples provided describe use of a horse radish peroxidase (HRP) labeled antibody, which is useful as a labeled marker indicator binding entity for this type of assay. When such an HRP-labeled marker indicator binding entity is employed, the amount of labeled marker indicator binding entity bound to the immobilized antigen can be determined by incubating the device in an HRP substrate for detecting the absorbance of the colored product that forms by action of the HRP enzyme. Such HRP substrates can include 2,2'-azinobis [3-ethylbenzothiazoline-6-sulfonic acid]-diammonium salt) (absorption at 410 nm and 650 nm), o-phenylenediamine dihydrochloride (absorbance maximum of 492 nm), or 3,3', 5,5'-tetramethylbenzidine (absorption maxima at 370 nm and 652 nm, which changes to an absorption maxima of 450 nm when sulfuric or phosphoric acid is added to stop the HRP reaction).

For example, when the optical density of test samples are measured and compared to a negative controls the following algorithms can be used to calculate either a sample/negative control (S/N) ratio or a percent inhibition using the following algorithms:

$$\text{Percent inhibition} = \left(\frac{OD \text{ negative control} - OD \text{ sample}}{OD \text{ negative control}}\right) \times 100$$

$$S/N \text{ ratio} = \left(\frac{OD \text{ sample}}{OD \text{ negative control}}\right)$$

If the S/N ratio was less than or equal to 0.6, the sample was classified as positive for the presence of anti-BoHV-1 antibodies (i.e., the animal from which the serum was obtained was infected with BoHV-1). If the S/N ratio was greater than 0.7, the sample was classified as negative for anti-BoHV-1 antibodies (i.e., the animal from which the serum was obtained was not infected with BoHV-1). If the SN ratio was between 0.6-0.7, then the sample was classified as suspect. The test can be repeated using new samples when a suspect sample is detected, or the animal can be vaccinated or treated for BoHV-1 infection.

In another example, a sandwich ELISA method can be employed, where a primary binding entity (e.g., anti-gE CT monoclonal antibody) is immobilized onto solid substrate (e.g., a 96-well plate), and a biological sample (blood, scrum, plasma, pharyngeal swab, urine) can be added to the substrate for contact and binding with the immobilized binding entity. After incubation, the plate is washed with an appropriate buffer, and then a labeled secondary binding entity (e.g., a labeled anti-gE CT binding entity) is reacted with the complex. When, for example, the label is HRP, biotin, peroxidase-labeled avidin (or streptavidin) and an appropriate reaction substrate (e.g., TBM) is added for color development. After a certain period of time, colorimetric determination is carried out at a specific wavelength (e.g., 450 nm).

Antibodies and/or Binding Entities

As used herein, "binding entities" include any molecule that can specifically bind to a gE cytoplasmic domain or peptide thereof. Each binding entity binds its target gE cytoplasmic domain or peptide thereof with specificity. Binding entities are typically binding regions of affinity molecules available in the biological sciences including, but not limited to, antibodies, antibody fragments, leucine zippers, histones, complementary determining regions (CDRs), single chain variable fragments (scFvs), receptors, ligands, aptamers, lectins, nucleic acid probes and the like. Binding entities can include binding regions that are generated, for example, from full sized versions of an affinity molecule, fragments of an affinity molecule, or the smallest portion of the affinity molecule providing binding that is useful in the detection of a target of interest (a gE cytoplasmic domain or peptide thereof).

The methods, compositions, devices and kits described herein can include binding entities which are members of the immunoglobulin family of proteins, or derivatives thereof. For example, the binding entity can be a complete immunoglobulin or antibody, a fragment, a single chain variable fragment (scFv), a heavy or light chain variable region, a CDR peptide sequence, and/or the like.

As used herein, "antibody" refers to an immunoglobulin molecule, and fragments thereof, which are immunologically reactive with a particular antigen. The term "antibodies" refers to a plurality of such molecules and is not limited to homogeneous populations of a single type of antibody. The term "antibody" also includes genetically engineered forms such as chimeric antibodies, heteroconjugate antibodies (e.g., bispecific antibodies), and recombinant single chain Fv fragments (scFv), and disulfide stabilized (dsFv) Fv fragments (sec, for example U.S. Pat. No. 5,747,654). The term "antibody" also includes antigen binding forms of antibodies (e.g., Fab', F(ab')2, Fab, Fv and IgG. See also, Pierce Catalog and Handbook, 1994-1995 (Pierce Chemical Co., Rockford, Ill.). The term "antibody," includes immunologically-active fragment of an immunoglobulin molecule such as the Fab or F(ab')2 fragment generated by, for example, cleavage of the antibody with an enzyme such as pepsin or co-expression of an antibody light chain and an antibody heavy chain in bacteria, yeast, insect cell or mammalian cell. The antibody can also be an IgG, IgD, IgA, IgE or IgM antibody.

Antibodies for use in the methods, compositions, kits and devices described herein can be obtained commercially or can be generated by available methods. Methods of making binding entities, antibodies, and antibody fragments are available in the art (see for example, Harlow and Lane, Antibodies: A Laboratory Manual, Cold Spring Harbor Laboratory, New York, (1988), specifically incorporated herein by reference in its entirety). For example, antibodies suitable for use the devices can be obtained by immunizing an animal such as a rabbit, goat, sheep, horse, or guinea pig. Such antibodies are present in the blood (e.g., serum) of immunized animals.

Antibody fragments can be prepared by proteolytic hydrolysis of the antibody or by expression of nucleic acids encoding the antibody fragment in a suitable host. Antibody fragments can be obtained by pepsin or papain digestion of whole antibodies conventional methods. For example, antibody fragments can be produced by enzymatic cleavage of antibodies with pepsin to provide a 5S fragment described as F(ab')2. This fragment can be further cleaved using a thiol reducing agent, and optionally using a blocking group for the sulfhydryl groups resulting from cleavage of disulfide linkages, to produce 3.5S Fab' monovalent fragments. Alternatively, enzymatic cleavage using pepsin produces two monovalent Fab' fragments and an Fc fragment directly. These methods are described, for example, in U.S. Pat. Nos. 4,036,945 and 4,331,647, and references contained therein. These patents are hereby incorporated herein by reference in their entireties.

A number of proteins can serve as protein scaffolds to which binding domains can be attached and thereby form a suitable binding entity. The binding domains bind or interact with gE cytoplasmic domains while the protein scaffold merely holds and stabilizes the binding domains so that they can bind. A number of protein scaffolds can be used. For example, phage capsid proteins can be used. See Review in Clackson & Wells, Trends Biotechnol. 12:173-184 (1994). Phage capsid proteins have been used as scaffolds for displaying random peptide sequences, including bovine pancreatic trypsin inhibitor (Roberts et al., PNAS 89:2429-2433 (1992)), human growth hormone (Lowman et al., Biochemistry 30:10832-10838 (1991)), Venturini et al., Protein Peptide Letters 1:70-75 (1994)), and the IgG binding domain of *Streptococcus* (O'Neil et al., Techniques in Protein Chemistry V (Crabb, L, ed.) pp. 517-524, Academic Press, San Diego (1994)). These scaffolds have displayed a single randomized loop or region that can be modified to include binding domains for the gE cytoplasmic domain or a peptide thereof.

Fibronectin type III domain has also been used as a protein scaffold to serve as a binding entity platform. Fibronectin type III is part of a large subfamily (Fn3 family or s-type Ig family) of the immunoglobulin superfamily. Sequences, vectors and cloning procedures for using such a fibronectin type III domain as a protein scaffold portion of a binding entity (e.g. that includes CDR peptides) are provided, for example, in U.S. Patent Application Publication 20020019517. See also, Bork, P. & Doolittle, R. F. (1992) Proposed acquisition of an animal protein domain by bacteria. Proc. Natl. Acad. Sci. USA 89, 8990-8994; Jones, E. Y. The immunoglobulin superfamily Curr. Opinion Struct. Biol. 3, 846-852 (1993); Bork, P., Hom, L. & Sander, C. (1994) The immunoglobulin fold. Structural classification, sequence patterns and common core. J. Mol. Biol. 242, 309-320; Campbell, I. D. & Spitzfaden, C. (1994) Building proteins with fibronectin type III modules Structure 2, 233-337; Harpez, Y. & Chothia, C. (1994).

It can be useful to employ a binding entity that binds to a gE cytoplasmic domain or peptide thereof with specificity. For example, the binding entity can have an affinity for an gE cytoplasmic domain or peptide thereof where the affinity is about $1\times10^{7}$ $M^{-1}$ to about $1\times10^{10}$ $M^{-1}$, or about $1\times10^{8}$ M to about $1\times10^{9}$ $M^{-1}$. For example, the affinity can be at least about $1\times10^{7}$ $M^{-1}$, at least about $1\times10^{8}$ $M^{-1}$, at least about $1\times10^{9}$ $M^{-1}$, or at least about $1\times10^{10}$ $M^{-1}$. The affinity of a binding entity can be measured by detecting and quantifying the formation of a binding entity-gE cytoplasmic domain complex (or a binding entity-gE cytoplasmic domain peptide complex), generally referred to as an antigen-antibody complex [Ag–Ab]. The formation of such an antigen-antibody complex [Ag–Ab] is illustrated by the following reaction.

$$Ab+Ag \rightleftharpoons AbAg$$

The formation of such an Ag-Ab complex is therefore at equilibrium with its dissociation, and the equilibrium association constant (KA) of the complex can be calculated as follows:

$$KA=1/kd=[Ag-Ab]/[Ag][Ab]$$

As used herein, the term "binds specifically" or "specifically binds," in reference to a binding entity or antibody interaction with an gE cytoplasmic domain or peptide thereof, means that the binding entity or antibody binds with a particular antigen (e.g., gE cytoplasmic domain or peptide thereof with any of SEQ ID NO:5-45) without substantially binding to other BoHV-1 proteins or peptides thereof (including the non-cytoplasmic tail portion of the gE protein).

For example, in some embodiments, binding entities can be employed in the methods, compositions, kits and devices described herein that bind with greater affinity or selectivity to gE cytoplasmic domain peptide (such as one with SEQ ID NO:45, or any of SEQ ID NOs: 5-44) than the affinity or selectivity of the binding entity for a full-length gE cytoplasmic domain (e.g. with SEQ TD NO:1 or 4), or vice versa. For example, binding entities can be employed in the methods, compositions, kits and devices described herein that bind to gE cytoplasmic tail peptide (such as one with any of SEQ TD NOs:5-45) with at least 50% or greater affinity (or selectivity), or 60% greater affinity (or selectivity), or 70% greater affinity (or selectivity), or 80% greater affinity (or selectivity), or 85% greater affinity (or selectivity), or 90% greater affinity (or selectivity), or 95% greater affinity (or selectivity) than to a gC cytoplasmic tail domain with SEQ ID NO:1 or 4.

Similarly, for example, a binding entities can be employed in the methods, compositions, kits and devices described herein that bind with greater affinity or selectivity to a gE cytoplasmic tail domain with SEQ ID NO:1 or 4, than to a peptide with any of SEQ ID NO:5-45. For example, the binding entity can bind to gE cytoplasmic tail domain with SEQ ID NO:1 or 4 with at least 50% or greater affinity (or selectivity), or 60% greater affinity (or selectivity), or 70% greater affinity (or selectivity), or 80% greater affinity (or selectivity), or 85% greater affinity (or selectivity), or 90% greater affinity (or selectivity), or 95% greater affinity (or selectivity) than the binding entity binds to a peptide any of SEQ ID NO:5-45.

Binding entities can be separated from impurities before incorporation into the compositions, kits or devices. For example, the binding entities can be purified or isolated using purification methods such as electrophoretic, molecular, immunological and chromatographic techniques, including ion exchange, hydrophobic, affinity, and reverse-phase HPLC chromatography, and chromatofocusing, and the like. The degree of purification necessary will vary depending on the contaminants present with the binding entities. In some instances no purification will be necessary (e.g., when binding entities are commercially available and provided in purified form).

Antibodies directed against gE cytoplasmic domain with SEQ ID NO:1 or 4; or against a gE cytoplasmic domain peptide with any of SEQ ID NO:5-45 are often monoclonal antibodies.

A monoclonal antibody is a population of molecules having a common antigen binding site that binds specifically with a particular antigenic epitope. A monoclonal antibody can be obtained by selecting an antibody-producing cell from a mammal that has been immunized with a selected antigen such as a gE cytoplasmic domain with SEQ ID NO:1 or 4, or a peptide thereof with any of SEQ ID NO:5-45, and fusing the antibody-producing cell, e.g. a B cell, with a myeloma to generate an antibody-producing hybridoma. A monoclonal antibody can also be obtained by screening a recombinant combinatorial library such as an antibody phage display library. See, for example, PHAGE DISPLAY—A LABORATORY MANUAL, Barbas, et al., eds. Cold Spring Harbor Laboratory Press, Cold Spring Harbor, N.Y., 2001; and Kontermann & Dübel, ANTIBODY ENGINEERING, Heidelberg: Springer-Verlag. Berlin, 2001. Techniques for preparing monoclonal antibody-secreting hybridoma cells are also described, for example, by Kohler and Milstein, Nature 256:495-97 (1975) and Kozbor et al. Immunol Today 4: 72 (1983).

A monoclonal antibody against a gE cytoplasmic domain or peptide thereof can also be prepared using other methods available in the art. For example, the antibodies can be obtained by screening of a recombinant combinatorial immunoglobulin library using a selected gE cytoplasmic domain or peptide thereof (e.g., any of SEQ ID NO:1, 4, 5-44 or 45) Immunoglobulins that selectively bind to a selected gE cytoplasmic domain or peptide thereof can be produced by recombinant expression from cells encoding the immunoglobulin of interest.

The antibodies can be evaluated for affinity to a selected against gE cytoplasmic domain or peptide thereof using standard procedures including, for example, enzyme linked immunosorbant assay (ELISA) to determine antibody titer, and protein A chromatography to obtain the antibody-containing an IgG fraction.

Another method for generating antibodies involves a Selected Lymphocyte Antibody Method (SLAM). The SLAM technology permits the generation, isolation and manipulation of monoclonal antibodies without needing to generate a hybridoma. The methodology principally involves the growth of antibody forming cells, the physical selection of specifically selected antibody forming cells, the isolation of the genes encoding the antibody and the subsequent cloning and expression of those genes.

The nucleic acids encoding the antibodies can be mutated to optimize the affinity, selectivity, binding strength or other desirable property of an antibody. A mutant antibody refers to an amino acid sequence variant of an antibody. In general, one or more of the amino acid residues in the mutant antibody is different from what is present in the reference antibody. Such mutant antibodies necessarily have less than 100% sequence identity or similarity with the reference amino acid sequence. In general, mutant antibodies have at least 75% amino acid sequence identity or similarity with the amino acid sequence of either the heavy or light chain variable domain of the reference antibody. Preferably, mutant antibodies have at least 80%, more preferably at least 85%, even more preferably at least 90%, and most preferably at least 95% amino acid sequence identity or similarity with the amino acid sequence of either the heavy or light chain variable domain of the reference antibody.

Labels

A variety of different labels can be used in the methods, compositions, binding entities, kits, and devices described herein. Labels can be covalently attached to any of the binding entities, primers or probes described herein. Alternatively, the labels can non-covalently associate with a hybridized probe or primer that is specifically bound to a target nucleic acid (e.g., an mRNA encoding a gE cytoplasmic domain or peptide thereof). Similarly, a label can be non-covalently or indirectly bound to a binding entity. For example, the label can be an enzyme substrate that changes into a detectable (e.g., colored) product when exposed to an enzyme. Alternatively, the label can be an enzyme that generates a colored signal when exposed to a substrate.

So called "direct labels" are detectable labels that are directly attached to or incorporated into a binding entity that then can bind to an gE cytoplasmic domain or peptide thereof. In contrast, so-called "indirect labels" are joined to a complex formed between a gE cytoplasmic domain or peptide thereof, and a binding entity after complex formation. For example, an indirect label can be attached to a secondary antibody that binds to a different epitope on a gE cytoplasmic domain or peptide thereof, than does a primary antibody. In another example, the label can be attached to a secondary antibody that binds to a primary antibody that is already bound to a gE cytoplasmic domain or peptide thereof.

Examples of labels include, but not limited to, fluorophores, chromophores, radiophores, enzymes, enzymatic substrates, enzymatic tags, antibodies, chemiluminescence, electroluminescence, and affinity labels. One of skill in the art will recognize that these and other labels can be used with success in this invention. Examples of enzyme labels include enzymes such as urease, alkaline phosphatase, or peroxidase to mention a few. Colorimetric indicator substrates can be employed to provide a detection means visible to the human eye or spectrophotometrically. Examples of fluorophores include, but are not limited to, Alexa 350, Alexa 430, AMCA, BODIPY 630/650, BODIPY 650/665, BODIPY-FL, BODIPY-R6G, BODIPY-TMR, BODIPY-TRX, Cascade Blue, Cy2, Cy3, Cy5, 6-FAM, Fluorescein, HEX, 6-JOE, Oregon Green 488, Oregon Green 500, Oregon Green 514, Pacific Blue, REG, Rhodamine Green, Rhodamine Red, ROX, TAMRA, TET, Tetramethylrhodamine, and Texas Red.

Means of detecting such labels are well known to those of skill in the art. For example, fluorescent markers may be detected using a microscope, photodetector or fluorimeter to detect emitted light. In still further examples, enzymatic labels can be detected by providing the enzyme with a substrate and detecting the reaction product produced by the action of the enzyme on the substrate, and colorimetric labels are detected by simply visualizing the colored label or reaction product; or by use of spectrometer.

Immunological Assay Device

A device for detecting BoHV-1 infection is shown in FIG. 7. FIG. 7A shows a schematic diagram of a device with an elongated housing 10 that contains a lateral flow strip 20. The lateral flow strip 20 extends substantially the entire length of housing 10. The lateral flow strip 20 is divided into a sample application area 40 positioned below a sample introduction port 30, an antigen-antibody conjugation site 50, a capture area 60, and a distal absorbent pad 70. The antigen-antibody conjugation site 50 can have mobile antigens 55 (e.g, a glycoprotein E cytoplasmic tail or peptide thereof). The flow strip 20 can also have a backing 80. The mobile antigen 55 in the antigen-antibody conjugation site 50 can be labeled antigens (such as gold-conjugated antigen) that can react with and bind to antibodies in a test sample from an animal. A flow path along the lateral flow strip 20 passes from the sample application area 40, through the antigen-antibody conjugation site 50, into the capture area 60. Immobilized binding entities such as an antibody that recognizes the a constant region of bovine antibodies, are positioned on capture area 60. The mobile antigens 55 can bind one or more antibodies that may be present in a test sample and the liquid flow can transport a conjugate formed between a mobile antigen and an antibody to the capture area 60, where immobilized binding entities can capture the antigen-antibody conjugates and concentrate the label in the capture area 60.

The mobile antigens 55 without a bound antibody pass through the capture area 60 and are eventually collected in the distal absorbent pad 70.

The lateral flow strip 20 can also include a reaction verification or control area 90. Such a control area 90 (e.g., configured as line) can be slightly distal to the capture area 60. The reaction verification or control area 90 illustrates to a user that the test has been performed. Prior to the test being performed, the reaction verification or control area 90 is not visible. However, when the test is performed by placing a fluid sample on the sample application area 40, the reaction verification or control area 90 can become visible as the sample flows through the capture area 60 and to the distal absorbent pad 70. For example, the reaction verification or control area 90 can become visible due to a chemical reacting with any component of the sample or simply due to the presence of moisture in the sample.

Quantitative results can be ascertained based on the magnitude of the identifiable signal from the capture area 60 after application of a sample to a sample introduction port 30. For example, in FIG. 7B a signal represented by a series of asterisks (***) is present in the capture area 60. The signal can be identified by visual inspection of the device, and/or the signal can be recorded and/or processed by a detector or a smart device. Such a smart device can be a small pocket computer, a laptop, a netbook, a desktop computer, or a smart phone. For example, the subject can display and/or record the results by taking a photograph of the detection device after testing by use of a smart device. The smart device can be configured to interpret the results by detecting the type and/or strength of a signal in the capture area 60** of a detection device.

Such a lateral flow device can be small enough for transportation in a pocket, mobile lab pack, backpack, or satchel. For example, lateral flow devices can be about 1 to 3 inches long and about 0.25 to about 1.5 inches wide. In general, the lateral flow devices are thin, having a depth of only about 0.1 to 0.75 inches.

Another device that can be used to detect BoHV-1 infection is a direct-charge transfer conductometric biosensor. Such direct-charge transfer conductometric biosensors are similar in structure to lateral flow devices and can be provided in a package that is small, for example, no larger than a pack of gum. Direct-charge transfer conductometric biosensors can employ immobilized antigen and polyaniline (emeraldine salt) as a transducer for detection. The antigen can be a glycoprotein E cytoplasmic tail polypeptide or peptide thereof) that can bind to anti-BoHV-1 antibodies that may be present in a test sample. Electron charge flow is aided through conductive polyaniline, to generate an electronic signal that can be recorded by a data collection system.

The biosensor architecture can be similar to a lateral flow device. Polyaniline bound to mobile antigen can first capture anti-BoHV-1 antibodies in a test sample, if present, to form a complex between the mobile antigen molecules and the antibodies. The complex can flow by capillary action to a capture site in the device where a complex can form with immobilized antibodies that bind to the anti-BoHV-1 antibodies. Such interaction provides a direct electron charge flow to generate a resistance signal that can be observed and/or recorded. The device is easy to use, and provides fast but sensitive results. See, e.g., Pal et al., Biosens. Bioelectron. 22 (9-10): 2329-36 (2007) (which is incorporated herein by reference in its entirety).

For example, electrically active polyaniline coated magnetic (EAPM) particles (e.g., nanoparticles) can be synthesized by coating the surface of gamma iron oxide cores with aniline monomers that are electrically active. The aniline monomers can be made to be electrically active, for example, by acid doping. Antigen molecules are adsorbed or covalently attached to the EAPM particles. The EAPM particles combined with the mobile antigen can be incorporated into a biosensor configured similar to a lateral flow device. Capillary flow of the complex between antibodies from the test sample and the antigen-EAPM particles. Detection of the complex formed between the antibodies and the antigen-EAPM particles occurs as the complex flows into a capture region where direct-charge transfer can occur across the EAPM particles.

Thus, to form this type of device, two or more electrodes can be screen-printed onto a solid substrate (e.g., paper, nitrocellulose or other convenient substrate), where the distance between the electrodes is sufficient to isolate each electrode from another until charge transfer occur across the EAPM particles in the capture region between the electrodes. The surface of a solid support (e.g. a nitrocellulose membrane) can be modified by a crosslinking agent such as glutaraldehyde to immobilize a binding entity (e.g., that reacts with antibodies in the test sample) within a capture region of the biosensor. The mobile antigen EAPM particles with any bound antibodies are drawn by capillary action to the capture region. The polyaniline acts as an electric signal transducer that signals binding between the mobile antigen-antibody EAPM particles and the immobilized binding entities. Such an electrical response can be measured by pulse mode measurement, which provides a quantitative measure of the amount of anti-BoHV-1 antibodies bound to the capture site.

For example, FIG. 7C is a schematic diagram of a schematic diagram of a direct-charge transfer conductometric biosensor with two electrodes 65 and 67, that can transfer a charge across the EAPM particles in the capture region 60 between the electrodes. FIG. 7D schematically illustrates collection of EAPM particles (***) in the capture region 60** between the electrodes.

Infection of BoHV-1 call be identified by visual inspection of the device and/or by the transfer of charge between the electrodes that provides an electrical signal communicating whether or not BoHV-1 infection is present. The signal can also be transmitted via a transmitter 95 to a receiver or smart device (e.g., a small pocket computer, a laptop, a netbook, a desktop computer, or a smart phone), which can receive the results, record the results, and alert personnel that a BoHV-1 infection has been detected.

Another detection device that can be employed to detect BoHV-1 infection utilizes Radio Frequency Identification (RFID), where tags ("smart labels") provide a signal to a handheld or stationary reader. Such RFID detection devices can be provided in a package that is the approximately the same size as a pack of gum or smaller. The radio frequency tags can be of various shapes, sizes, and readout ranges. For example, the tags can be minute, and the detection strips with the tags can be thin and flexible. In some cases, radio frequency identification devices can have tags on a paper or plastic strip. Such RFID tags can contain silicon chips and, in some embodiments, antennas. Passive tags require no internal power source, whereas active tags require an internal power source.

The configuration of an RFID-containing BoHV-1 detection device can be similar to a lateral flow device. For example, the RFID device can have a sample port into which a sample is loaded. Such a sample may comprise, for example, saliva, whole blood, plasma, serum, urine, lymph, etc. The sample can flow into a antigen-antibody conjugation site where antibodies in a test sample can bind to mobile RFID-labeled antigens. The sample passes (e.g., by capillary flow) into an RFID capture and identification zone, in which the RFID-antigen-antibody complexes are immobilized, for example, by binding to an immobilized binding entity that binds to bovine antibodies (e.g., to the constant region of bovine antibodies). The capture region is then subjected to RFID interrogation by an RFID detector. The unreacted RFID-labeled antigens (i.e., not bound to an antibody from the test sample) and other components of the sample pass through the RFID capture and identification zone into a radio frequency protected "waste" zone, which can have shielding to prevent RFID tags therein from being detected by the RFID detector. The detection of a particular RFID tag by the RFID detector is indicative that anti-BoHV-1 antibodies are present in the sample. See, e.g., US 20120269728 by Jen et al., which is specifically incorporated herein by reference in its entirety.

FIG. 7E is a schematic diagram illustrating a detection device that has RFID tags as labels on antigens 55. The device can have an unshielded antigen-antibody conjugation site 50, and shield 75 over distal absorbent pad 70, so that collection of RFID tags in the capture area 60 can transmit a radio signal (represented by ***, see FIG. 7**F). Such a signal indicates that one anti-BoHV-1 antibodies are present in the test sample and have been detected by the device.

A detector or reader can receive a passive or active tag signal from the RFID test strip. A Passive Reader Active Tag (PRAT) system has a passive reader that only receives radio signals from active tags (battery operated, transmit only). The reception range of a PRAT system reader can be adjusted from 1-2,000 feet, allowing some flexibility in the field. The detector or reader can be a smart device.

An Active Reader Passive Tag (ARPT) system has an active reader, which transmits interrogator signals and also receives authentication replies from passive tags. An Active Reader Active Tag (ARAT) system uses active tags awoken with an interrogator signal from the active reader. A variation of this system can involve use of a Battery Assisted Passive (BAP) tag which acts like a passive tag but has a small battery to power the tag's return reporting signal. The detector or reader can be a smart device, which can receive radio signals via Bluetooth transmission and/or reception.

Another device that can be used for determining the presence of BoHV-1 infection in a fluid sample is a test strip. The test strips can be provided in a roll, where a section of the roll is torn off for testing. Alternatively, the test strips can be provided in a package that is the approximately the same size as a pack of gum or smaller. The test strip can have one or more gE CT antigens (e.g., one or more with SEQ ID NOs:1, 4-44, and/or 45) immobilized thereon. A bodily fluid can be applied to the test strip and a signal can be detected when anti-BoHV-1 antibodies are present in the bodily fluid. To enhance the signal, the strip can optionally be placed in a development solution. The signal indicates that the sample is from an animal infected with BoHV-1.

FIG. 8 shows an example of a roll of test strips 100. The roll of test strips 100 has one or more types of immobilized antigens 110 that can specifically bind to anti-BoHV-1 antibodies that may be present in a test sample. A subject can tear a test strip segment 105 from the roll of test strips 100. The test sample (e.g. a bodily fluid such as serum, blood, saliva, mucus, or urine) can be applied anywhere along the test strip segment 105. A signal can be detected from the test strip when a test sample contains antibodies against BoHV-1. A rinsing liquid 120 (e.g., water or PBS) can be used to remove unbound materials after the sample has been applied to the test strip segment 105. The test strip segment 105 can optionally be immersed in one or more development solutions 130 that can be provided with roll of test strips 100. The signal can directly be detected or the strip can optionally be rinsed in a rinsing liquid 140 (e.g., water or PBS). The signal (e.g. a color) indicates that the sample is from an animal infected with BoHV-1. The roll test strip 100 can be elongated rectangular material wound into a roll. Segments 105 of the roll of test strips 100 are easily removed or torn from the roll without loss or changes in the detection properties of the materials that make up the roll of test strips 100. In certain examples, the roll of test strips 100 can be composed of paper, nitrocellulose, or other porous inert materials. The test strips can also be in the form of short strips (e.g., about 1 to 3 inches long), that are provided in a package that is the approximately the same size as a pack of gum or smaller.

The test strips can be flexible and readily transported as individual strips in a small package, or as a continuous roll of test strip material. The test strip can vary in width, thickness, and length. For example the test strip can be about 0.2 to about 1 inch wide. The test strip can be as thick as a piece of paper or somewhat thicker, for example, about 0.02 to about 0.5 inches thick. Individual strips can be about 1 inch to 3 inches long. A continuous roll test strip material can be of varying length, for example, a length that allows easy transportation in a pocket or handbag when rolled up.

The development solution(s) can contain reagents that recognize the antigen-antibody complex and that provide a visually detectable signal identifying that such a complex has formed. For example, a development solution can contain a secondary binding entity or antibody that binds to anti-BoHV-1 antibodies to form a ternary complex with an antigen-antibody immobilized on the test strip. The secondary binding entity or antibody can be linked to a visually detectable label, or it can be linked to an entity that can generate a visually detectable signal upon exposure to a substrate. For example, the secondary binding entity or antibody can be linked to an enzyme to produces a visually detectable signal upon exposure to a substrate for the enzyme.

Quantitative results can be ascertained based on the magnitude of the identifiable signal from the test strip segment 105 that has been treated as described above. A smart device can be used to display, record, graph, and/or interpret the results. For example, the methods described herein can include a step of photographing the results shown on the detection device using a smart device. The smart device can record, store, process, and display the results as well as graphic interpretations of the results.

Hence a variety of devices can be used to evaluate test samples for BoHV-1 infection.

Kits

To provide those skilled in the art with tools to use the present invention, the glycoprotein E cytoplasmic tail polypeptide or peptide (e.g., any polypeptide or peptide with SEQ ID NOs: 1, 4-44, 45, or a combination thereof) can be assembled into kits for the diagnosis, detection or confirmation of BoHV-1. The presence of antibodies reactive to glycoprotein E cytoplasmic tail polypeptide or peptide thereof (e.g., any polypeptide or peptide with SEQ ID NOs: 1, 4-44, 45, or a combination thereof) is used to identify animals infected with BoHV-1 and/or animals that would benefit from vaccination with the BoHV-1 tmv vaccine. The information provided is also used to direct the course of treatment. For example, if a subject is found to have antibodies against to glycoprotein E cytoplasmic tail polypeptides (e.g., SEQ TD NO:1 or 4) or peptides thereof, (e.g., any of SEQ ID NOs: 5-45) provide useful antigens for detection of antibodies that are circulating in BoHV-1 animals.

The kits can include a carrier means for the devices and reagents as well as other components of the kits. Such a carrier can be a box, a bag, a satchel, plastic carton (such as molded plastic or other clear packaging), wrapper (such as, a sealed or sealable plastic, paper, or metallic wrapper), or other container. In some examples, kit components will be enclosed in a single packaging unit, such as a box or other container, which packaging unit may have compartments into which one or more components of the kit can be placed. In other examples, a kit includes one or more containers, for instance vials, tubes, and the like that can separately contain, for example, one or nucleic acid probes, one or more binding entities, one or more devices, as well as positive and/or negative control samples or solutions.

For example, at least one of the containers can include at least BoHV-1 antigen such as a glycoprotein E cytoplasmic tail polypeptide (e.g., SEQ ID NO:1 or 4) or a peptide thereof (e.g., any of SEQ ID NOs: 5-45). In another embodiment, at least one of the containers can include at least one binding entity that binds with specificity or selectivity to the BoHV-1 glycoprotein E cytoplasmic tail polypeptide (e.g., SEQ ID NO:1 or 4) or a peptide thereof (e.g., any of SEQ ID NOs: 5-45). The binding entities, can be detectably labeled. For example, the binding entities can be packaged separately from the labels, and the label can be added to the binding entities, during or after performance of an assay for detecting BoHV-1.

Kits can also contain vials, needles, syringes, finger-prick devices, alcohol swabs, gauze squares, cotton balls, bandages, latex gloves, incubation trays with variable numbers of troughs, adhesive plate sealers, data reporting sheets, which may be useful for handling, collecting and/or processing biological samples. Kits may also optionally contain implements useful for introducing samples into an assay chamber or a cell capturing device, including, for example, droppers, Dispo-pipettes, capillary tubes, rubber bulbs (e.g., for capillary tubes), and the like. Other components can also be present in the kits such as disposal means for discarding used devices and/or other items used with the device (such as patient samples, etc.). Such disposal means can include, without limitation, containers that are capable of containing leakage from discarded materials, such as plastic, metal or other impermeable bags, boxes or containers.

The kits can include instructions for performing an assay such as an immunoassay.

Use of the methods, compositions, devices, and kits described herein facilitate early detection of BoHV-1 infection, and identify animals that should be vaccinated and/or treated for infection.

The following non-limited Examples illustrate some of the materials, methods, and experiments used in the development of the invention.

Example 1: Materials and Methods

This Example describes some of the materials and methods used in developing the invention.

Cells and Virus Strain.

The Madin-Darby bovine kidney (MDBK) cell line obtained from the American Type Culture Collection (Manassas, Va.) was maintained in Dulbecco's modified Eagle's medium (DMEM) supplemented with 5-10% heat-inactivated fetal bovine serum (FBS) (HyClone Laboratories, Inc., South Logan, Utah). The BHV-1 Cooper (Colorado-1) strain, obtained from the American Type Culture Collection (Cat #CRL-1390; Manassas, Va.), was propagated and titrated in MDBK cells as described by Chowdhury (Microbiol 52(1-2):β-23 (1996)).

The BoHV-1 tmv virus containing deletions of UL49.5 residues 30-32 and 80-96, gE cytoplasmic tail (CT) residues 452-575, and the entire Us9 gene, as well as the BoHV-1 gE-deleted virus with a deletion of the entire gE open reading frame, were constructed as described by Wei & Chowdhury, PloS one 6(10):e25742 (2011); and Brum et al. *J Neurovirol* 15(2):196-201 (2009)). The BoHV-1 Cooper (Colorado-1) strain (ATCC Cat #CRL-1390, Manassas, Va.) was used as the reference wild type strain.

Monoclonal/Polyclonal Antibodies.

Mouse anti His-tag MAb (Genscript Cat #A00186) and/or goat anti gE CT-specific antibody (Chowdhury et al., *Vaccine* 32(39):4909-4915 (2014)) goat anti mouse-HRP conjugated polyclonal antibody (Thermo Scientific) were used to confirm reactivity and specificity of the recombinant protein and MAb respectively.

Construction of a gE CT Domain-Expressing pET-43.1a Plasmid.

The amino acid sequence of residues 451-575 of the gE cytoplasmic tail (CT) is shown in FIG. 1B (SEQ ID NO:1). An *E. coli* codon-optimized nucleic acid segment (SEQ ID NO: 2) was synthesized that encodes the SEQ ID NO:1 gE CT polypeptide domain (FIG. 1C). This SEQ ID NO:2 nucleic acid segment was modified to generate the SEQ ID NO:3 nucleic acid that includes, at the 5' end, a Ndc I restriction site followed by a methionine codon and six histidine codons. At the 3' end, the SEQ ID NO:3 construct has a stop codon followed by XhoI restriction site (FIG. 1D). Hence, the SEQ ID NO:3 nucleic acid encodes the modified gE CT-His polypeptide (SEQ ID NO:4) shown in FIG. 1E. The 411 bp long NdeI/XhoI fragment (SEQ ID NO:3) was inserted into the NdeI-XhoI sites of pET-43.1a (Novagen) to create the pET-43.1a gE CT-His construct. The molecular weight of the *E. coli* expressed and purified gE CT-His was verified by SDS-PAGE.

Production and Characterization of gE CT-Specific Mouse Monoclonal Antibody.

The gE CT-His protein (SEQ ID NO:4) was expressed from the pET-43.1a gE CT-His construct within *E. coli*. Protein purification, immunization of mice, production of hybridomas, purification of the MAb 2H8F3 from the ascites fluid and conjugation of the MAb with HRP (horse reddish peroxidase) were performed by Genscript. Purification of gE CT-His from *E. coli*, immunoblotting analysis and generation of mouse monoclonal antibody (MAb).

The *E. coli* expressed gE CT-His protein (SEQ ID NO:4) was obtained from inclusion bodies, solubilized with 8M urea and purified in two steps by use of a Ni column and Superdex 200 (GE Healthcare). *E. coli*-expressed gE CT-His protein thus purified, was then tested for reactivity with anti-His antibody (Genscript cat. #A00186). Mice were immunized with the purified gE CT-His protein. Anti-His negative, gE CT-specific hybridomas were selected for further processing. Hybridomas producing gE CT-specific antibodies were selected for the production of mouse ascites. The 2H8F3 monoclonal antibody was thereby generated.

Western Blot Analysis of Recombinant gE CT-his Protein with gE CT-Specific MAb.

The gE CT-His antigen protein samples were separated on a SDS-PAGE (10% or 12%) and transferred onto a nitrocellulose membrane. The membrane was blocked in 5% skimmed milk in PBS and/or TBS for 1 hr at room temperature (RT), washed with 0.05% tween 20 in PBS (PBST) or TBS (TBST) and incubated with antibody (0.5 µg/ml diluted in PBS or TBS for 2-3 hours or overnight at room temperature). After washing, the membrane was incubated either with secondary antibody goat anti mouse HRP or with secondary antibody IRDyc800CW goat anti-mouse IgG at room temperature for 1 hour. After washing, the membrane was visualized either with Pierce ECL western blotting substrate/autoradiography or under Odyssey scanner (LI-COR, Odyssey V3.0).

Synthesis of Biotinylated, Overlapping Peptides, and Epitope Mapping ELISA.

Thirty nine 12-mer overlapping peptides (Table 1) spanning the entire 125 aa residues of gE CT (FIG. 1A-1B) were synthesized and biotinylated (Genscript).

TABLE 1

Peptides for Epitope Mapping

| No. | Peptide Sequence | SEQ ID NO: |
|---|---|---|
| 1 | ASQKRTYDILNP | 5 |
| 2 | KRTYDILNPFGP | 6 |
| 3 | YDILNPFGPVYT | 7 |
| 4 | LNPFGPVYTSLP | 8 |
| 5 | FGPVYTSLPTNE | 9 |
| 6 | VYTSLPTNEPLD | 10 |
| 7 | SLPTNEPLDVVV | 11 |
| 8 | TNEPLDVVVPVS | 12 |
| 9 | PLDVVVPVSDDE | 13 |
| 10 | VVVPVSDDEFSL | 14 |
| 11 | PVSDDEFSLDED | 15 |
| 12 | DDEFSLDEDSFA | 16 |
| 13 | FSLDEDSFADDD | 17 |
| 14 | DEDSFADDDSDD | 18 |
| 15 | SFADDDSDDDGP | 19 |
| 16 | DDDSDDDGPASN | 20 |
| 17 | SDDDGPASNPPA | 21 |
| 18 | DGPASNPPADAY | 22 |
| 19 | ASNPPADAYDLA | 23 |
| 20 | PPADAYDLAGAP | 24 |
| 21 | DAYDLAGAPEPT | 25 |
| 22 | DLAGAPEPTSGF | 26 |
| 23 | GAPEPTSGFARA | 27 |
| 24 | EPTSGFARAPAN | 28 |
| 25 | SGFARAPANGTR | 29 |
| 26 | ARAPANGTRSSR | 30 |
| 27 | PANGTRSSRSGF | 31 |
| 28 | GTRSSRSGFKVW | 32 |
| 29 | SSRSGFKVWFRD | 33 |
| 30 | SGFKVWFRDPLE | 34 |
| 31 | KVWFRDPLEDDA | 35 |
| 32 | FRDPLEDDAAPA | 36 |
| 33 | PLEDDAAPARTP | 37 |
| 34 | DDAAPARTPAAP | 38 |
| 35 | APARTPAAPDYT | 39 |
| 36 | RTPAAPDYTVVA | 40 |
| 37 | AAPDYTVVAARL | 41 |
| 38 | DYTVVAARLKSI | 42 |
| 39 | TVVAARLKSILR | 43 |

The biotinylated peptides (20 µg/ml) were immobilized onto 96-well microtiter plates pre-coated with 100 µl of 10 µg/ml streptavidin (NEB, Cat #A00160). In addition, a microtiter plate was coated with purified antigen protein gE CT-His (2 µg/ml) in 100 µl coating buffer at 4° C. overnight. The plates were then blocked with the blocking buffer (5% skimmed milk in PBS) at 37° C. for 2 hours. After washing the plate with washing buffer (PBS with 0.05% tween), 100 µl of 1 µg/ml MAb 2H8F3 was added to the plates and incubated at 37° C. for 2 hours. The plates were washed with washing buffer (PBST) and then incubated with 100 µl of secondary antibody (0.1 µg/ml goat anti-mouse IgG [HRP]) at 37° C. for 1 hour. After washing, the reaction was developed with 100 µl TMB substrate for 10 minutes at room temperature. The reaction was stopped by adding 100 µl of 1 M HCl. The absorbance of each well was measured at 450 nm using a spectrometer. An uncoated well was used as a blank control. The peptide library incubated with the secondary antibody only was also used as a negative control.

Infection of Calves.

Animal infection, handling, sample collection and euthanasia protocols were previously approved by the LSU Institutional Animal Care and Use Committee. To determine the differential serological marker properties of BoHV-tmv in infected/vaccinated calves compared with the BoHV-1 gE-deleted and BoHV-1 wt-infected calves, twelve BoHV-1 and BVDV negative, 4-month-old cross-bred bull calves were selected and randomly assigned into three groups. The first group consisted of three calves infected with wild type BoHV-1. The second group consisted of four calves immunized with the BoHV-1 gE-deleted vaccine. The third group consisted of five calves immunized with the BoHV-1 tmv vaccine. Calves in each group were housed at the LSU large animal isolation facility well isolated from each other in separate rooms, where 2-3 calves were maintained per room. Calves in each group were infected intranasally with $1 \times 10^7$ PFUs per nostril of the respective virus or vaccine. Thus, each calve received $2 \times 10^7$ PFUs of virus/vaccine. Following infection, nasal swabs were collected every other day until day 10 post-infection. Sera samples were collected at days 0, and 28 days post-infection, then aliquoted and stored at $-80°$ C. until further analysis.

Competitive ELISA Tests.

Competitive ELISA was performed to detect the presence or absence of gE CT antibodies among the three groups of calve sera: wild type (WT) BoHV-1 infected calve scrum, BoHV-1 tmv vaccinated calve scrum, and gE deleted (gEΔ) vaccinated calve serum. This was accomplished by collecting samples of WT, BoHV-1 tmv, and gEΔ calf sera at day 0 (prior to infection) and 28 days post infection (dpi), then testing for the presence of anti-gE antibodies.

An ELISA plate (Costar, #3590) was coated overnight at 4° C. with 200 μl/well (approx. 100 ng) of gE CT-His protein antigen in a coating buffer (30 mM $Na_2CO_3$/70 mM $NaHCO_3$ pH9.6). After washing with 0.05% Tween 20-PBS pH 7.4 (PBST) followed by 1×PBS pH 7.4 (PBS), the plates were blocked with 1% bovine serum albumin (BSA) in PBS at 37° C. for 2 hours. After washing, the plates were incubated overnight at 4° C. with 100 μl of calf sera diluted 1:1 in 0.1% PBST. The next day, the plates were washed and incubated for 1 hour at room temperature with 100 μl of HRP conjugated anti-BoHV-1 gE CT-specific Mab 2H8F3 antibodies diluted 1:10,000 in 0.05% PBST/well. Plates were washed and 150 μl of TMB substrate was added to each well. The plates were incubated at room temperature in the dark for 15 minutes, and then 75 μl of 1M $H_2SO_4$ was added to stop the reaction. The optical density (OD) of each well was read at 450 nm using a microtiter plate reader (SpectraMax M2, Molecular Devices with Soft Max Pro 4.8).

Statistical Analysis: The SAS® (version 9.4, SAS Institute, Cary, N.C.) mixed procedure was used to analyze the competitive ELISA data with a repeated measures analysis of variance in a mixed effects model. Fixed effects included Sample, DPI and the interaction Sample*DPT. The random effect in the model was Calf (Sample). When overall differences were found, post hoc comparisons were made with pairwise "t" tests of least-squares means. All comparisons were considered significant at $p \leq 0.05$.

Figures 2A, 2B, 2C, 2D:
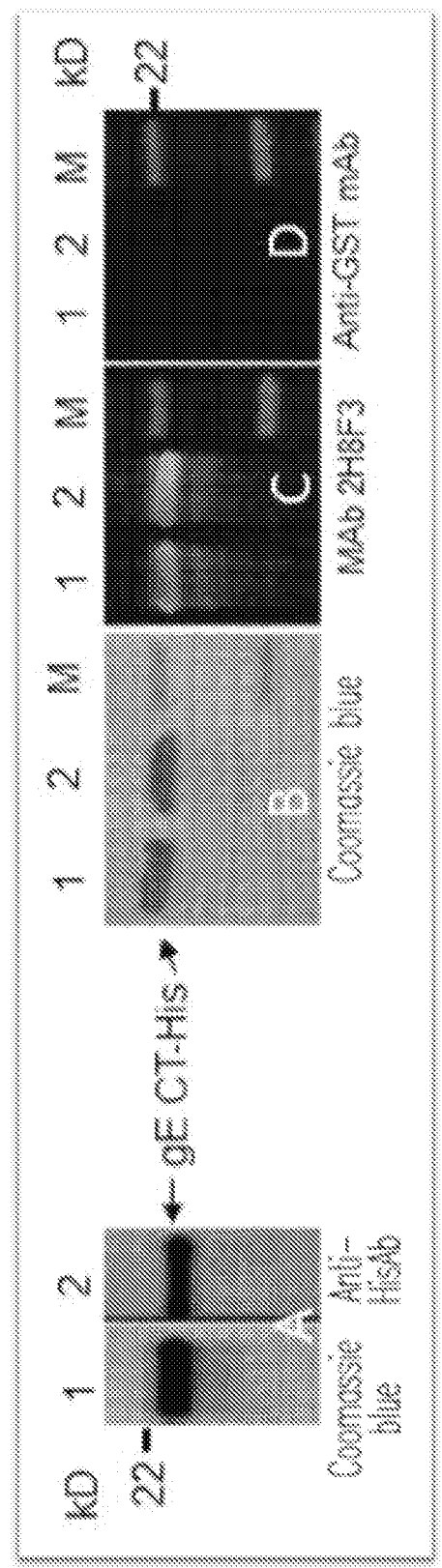
Figure 3:
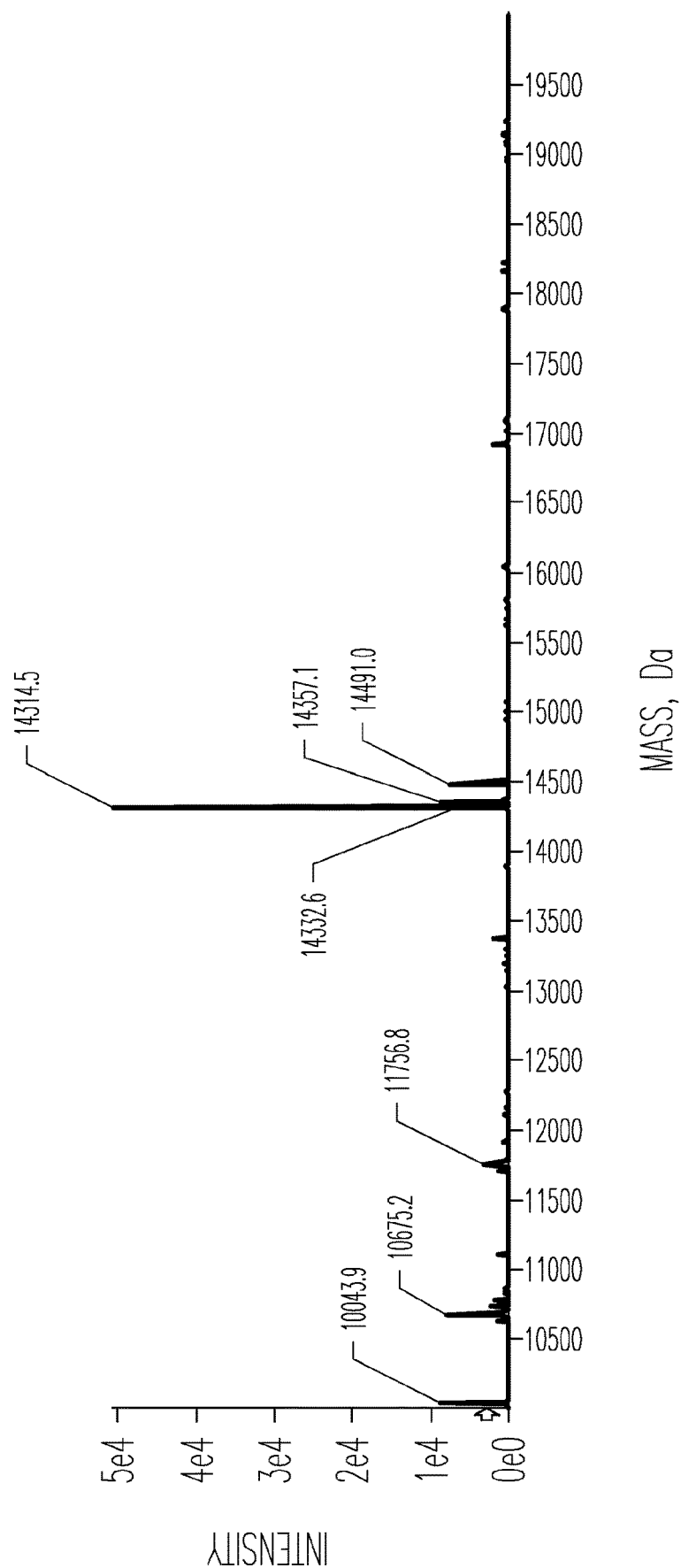
Figure 4B:
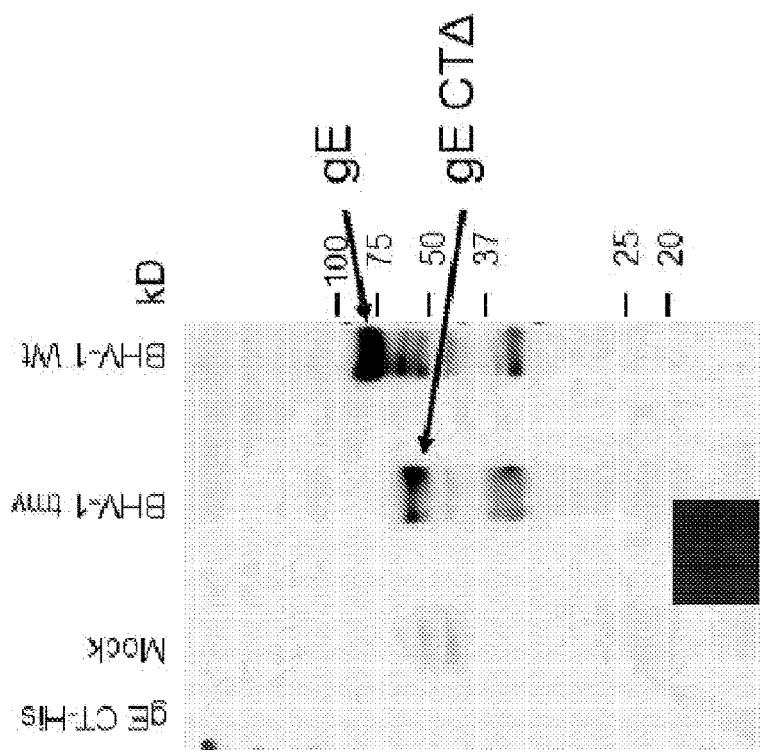
Figure 4A:
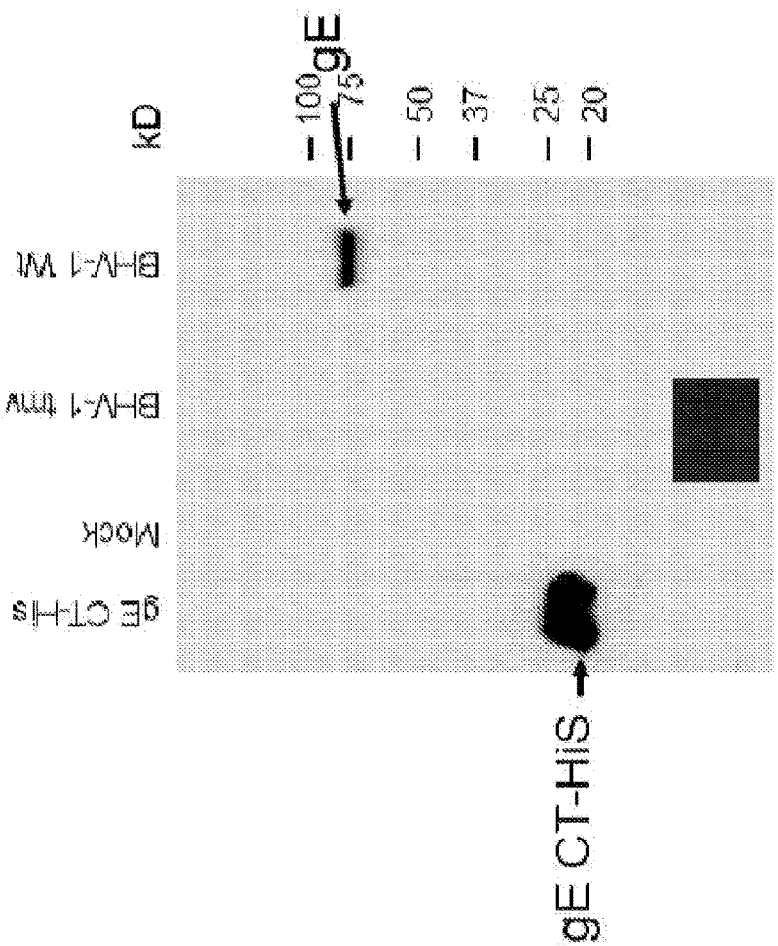
Figure 5:
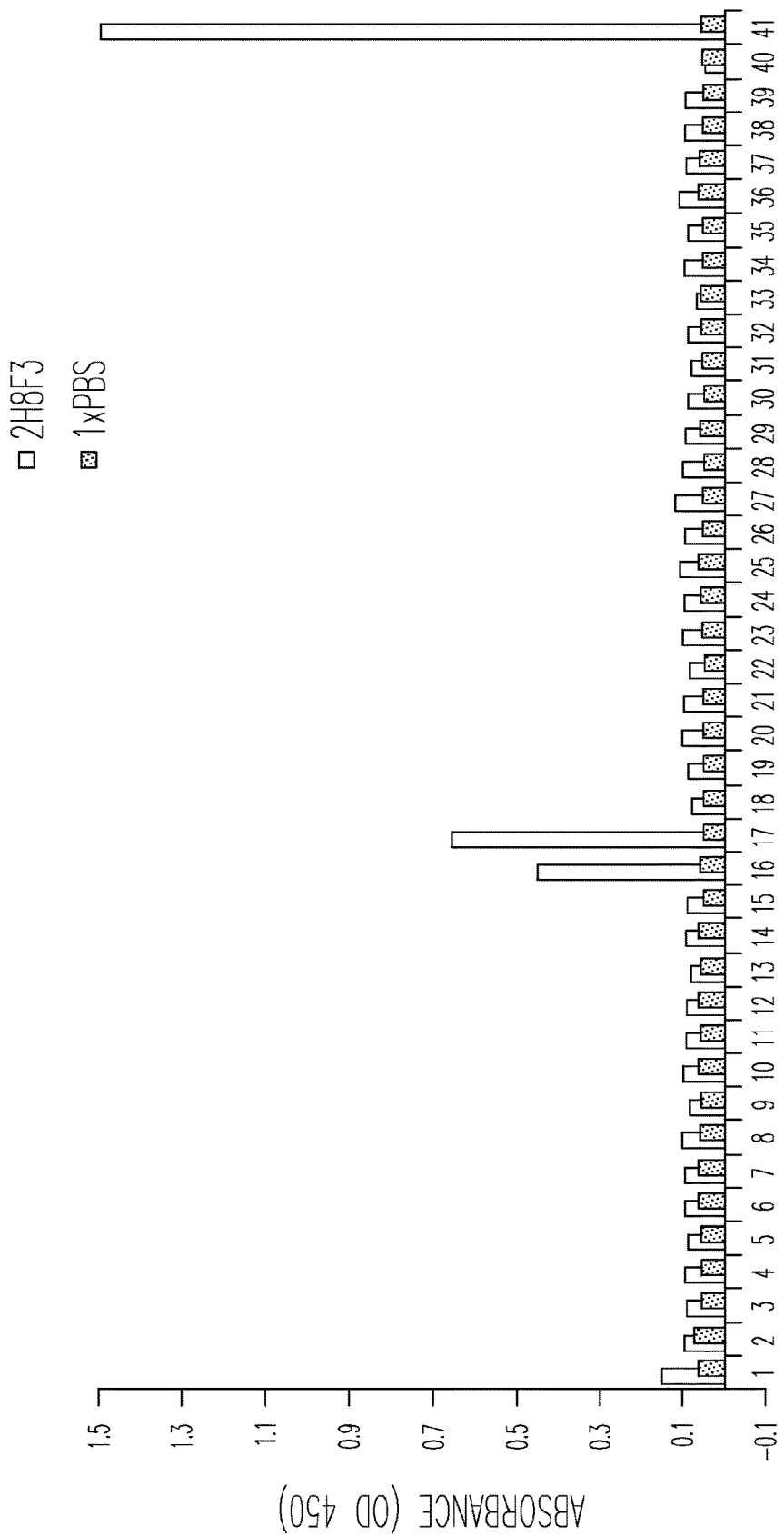
Figure 6:
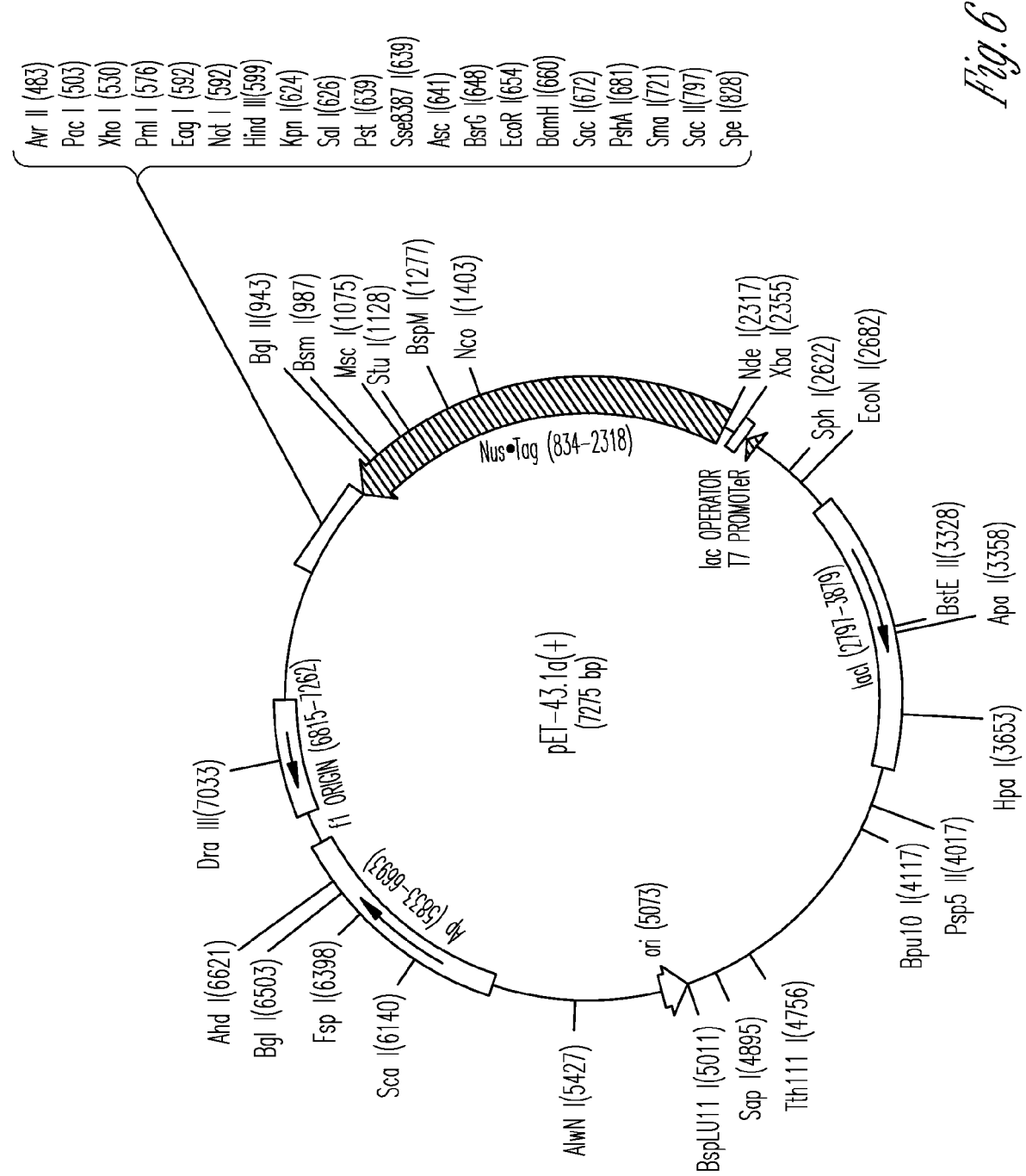

Example 2: gE Cytoplasmic Tail-Specific Antibody Distinguishes Wild Type BoHV-1 Virus-Infected from BoHV-1 Tmv-Infected Cells As shown in FIG. 1E, the molecular weight of the *E. coli* expressed recombinant gE CT-His protein is predicted to be 14.3 kD using the calculator provided by ExPASy.org Immunoblotting experiments with the anti-His antibody indicated that gE CT-His protein expressed in *E. coli* from the pET-43.1a gE CT-His construct had a slightly higher molecular weight than the predicted 14.3 kD (FIG. 2A). Therefore, MALIDI-TOF mass spec analysis was performed to assess the actual mass of the expressed protein. Such analysis showed that the molecular weight of the expressed gE CT-His protein was very similar as the predicted molecular weight (FIG. 3).

Subsequently, a BoHV-1 gE CT-specific mouse monoclonal antibody (MAb2H8F3) was generated using Genscript technology by immunizing mice with the gE CT-His protein as antigen. Further immunoblotting analysis demonstrated that the same *E. coli*-expressed gE CT-His protein shown in FIG. 2A-B is recognized by MAb2H8F3 (FIG. 2C) but not by an anti GST-specific antibody (FIG. 2D).

Additionally, the MAb2H8F3 antibody reacted specifically with a 94 kD band corresponding to BoHV-1 wild type gE that had been expressed by wild type BoHV-1 virus-infected cells. However, the MAb2H8F3 antibody did not react with a 68 kD band expressed by BoHV-1 tmv-infected cells (FIG. 2E) because the BoHV-1 tmv vaccine lacks the gE CT domain.

These results demonstrate that the MAb2H8F3 antibody specifically recognizes an epitope located within the 125 amino acids of the gE cytoplasmic tail. More significantly, these results also indicate that BoHV-1 tmv-infected cells can be distinguished from wild type BoHV-1 virus-infected cells, for example, by using the MAb2H8F3 antibody to detect wild type BoHV-1 or by using the gE cytoplasmic tail as an antigen to detect antibodies that may be in the serum of BoHV-1 virus-infected animals.

Example 3: Epitope Recognized by the MAb2H8F3 Antibody

To map the epitope that the specified by the MAb2H8F3 specifically recognizes in the BoHV-1 gE CT domain, thirty nine overlapping 12-mer peptides (Table 1) spanning the entire 125 amino acid cytoplasmic tail of the gE protein (SEQ ID NO:1) were generated and analyzed for binding with the gE CT-specific MAb2H8F3 antibody.

The ELISA was performed with plates where each well was coated with a separate 12-mer peptide. One plate was reacted with the gE CT-specific MAb2H8F3 antibody. A second plate with wells coated by the peptide of the library was incubated with the secondary antibody only as a negative control. In addition, well number 40 contained streptavidin (no peptide) as blank control and well number 41 contained the *E. coli* expressed recombinant gE CT-His polypeptide (SEQ ID NO:4).

The ELISA test results presented in Table 2 and FIG. 3 show that the MAb2H8F3 reacted specifically with the two overlapping peptides:

Peptide$_{496}$DDSDDDGPASN$_{507}$ (SEQ ID NO:20; peptide 16 in Table 1) and

Peptide $_{499}$SDDDGPASNPPA$_{510}$ (SEQ ID NO:21; peptide 17 in Table 1).

Therefore, the epitope bound by the MAb2H8F3 antibody maps within gE amino acid positions 499-507.

TABLE 2

ELISA results of epitope mapping for MAb 2H8F3.

| Peptide/Well No. | SEQ ID NO: | MAb2H8F3 O.D. 450 nm | Secondary Ab (only) O.D. 450 nm |
|---|---|---|---|
| 1 | 5 | 0.152 | 0.062 |
| 2 | 6 | 0.096 | 0.074 |
| 3 | 7 | 0.093 | 0.058 |
| 4 | 8 | 0.097 | 0.058 |
| 5 | 9 | 0.089 | 0.056 |
| 6 | 10 | 0.097 | 0.063 |
| 7 | 11 | 0.099 | 0.060 |
| 8 | 12 | 0.103 | 0.059 |
| 9 | 13 | 0.083 | 0.058 |
| 10 | 14 | 0.101 | 0.061 |
| 11 | 15 | 0.094 | 0.059 |
| 12 | 16 | 0.095 | 0.063 |
| 13 | 17 | 0.082 | 0.058 |
| 14 | 18 | 0.095 | 0.060 |
| 15 | 19 | 0.087 | 0.052 |
| 16 | 20 | 0.450 | 0.056 |
| 17 | 21 | 0.655 | 0.053 |
| 18 | 22 | 0.082 | 0.053 |
| 19 | 23 | 0.087 | 0.052 |
| 20 | 24 | 0.102 | 0.054 |
| 21 | 25 | 0.098 | 0.053 |
| 22 | 26 | 0.086 | 0.051 |
| 23 | 27 | 0.101 | 0.055 |
| 24 | 28 | 0.098 | 0.059 |
| 25 | 29 | 0.105 | 0.060 |
| 26 | 30 | 0.097 | 0.055 |
| 27 | 31 | 0.121 | 0.053 |
| 28 | 32 | 0.100 | 0.054 |
| 29 | 33 | 0.098 | 0.056 |
| 30 | 34 | 0.087 | 0.051 |
| 31 | 35 | 0.081 | 0.052 |
| 32 | 36 | 0.089 | 0.056 |
| 33 | 37 | 0.066 | 0.056 |
| 34 | 38 | 0.097 | 0.052 |
| 35 | 39 | 0.089 | 0.055 |
| 36 | 40 | 0.111 | 0.066 |
| 37 | 41 | 0.094 | 0.058 |
| 38 | 42 | 0.099 | 0.054 |
| 39 | 43 | 0.096 | 0.053 |
| 40 | — | 0.051 | 0.055 |
| 41 | 4 | 2.359 | 0.057 |

Analysis of the two peptide sequences (SEQ ID NOs: 20-21) demonstrate that the nine amino acids $_{499}$SDDDGPASN$_{507}$ (SEQ ID NO: 44) are common between the two overlapping peptides. Based on these results the epitope recognized by the MAb2H8F3 antibody within the gE CT domain is $_{499}$ESDDDGPASN$_{507}$ (SEQ ID NO:45). The MAb2H8F3 antibody is referred to herein as the HRP-conjugated indicator marker antibody

Example 4: Serological Assay for Distinguishing BoHV-1 WT-Infected Calves from BoHV-1 Tmv and/or gE-Deleted Virus-Infected Calves The direct ELISA test described above was optimized using a series of coating antigen concentrations and HRP-conjugated MAb2H8F3 dilutions. Based on these analyses (data not shown), the optimal amount of gE CT-His coating antigen and HRP-conjugated MAb 2H8F3 (indicator marker antibody) were selected to be 100 ng of gE CT-His antigen and 1:10,000 dilution of the HRP conjugated MAb, respectively.

The competitive ELISA method was performed as follows. Inactivated calve sera obtained prior to infection (day 0) and at 28 days post-infection were incubated in separate microtiter wells coated with the gE CT-His antigen. After such incubation, the HRP conjugated indicator marker antibody was added and the ELISA plates were again incubated. The wells were then washed, and the optical density at 450 nm of each sample well was determined. Inactivated, non-infected fetal calf serum (available commercially, Atlas biologicals), and hyper immune BoHV-1 wt-specific calf serum (BoHV-1 HI) produced by multiple buster intermuscular immunizations using purified BoHV-1 as antigen) were used as negative and positive controls, respectively.

The measured optical density of test samples and controls at 450 nm was used to calculate either a sample/negative control (S/N) ratio or a percent inhibition using the following algorithms:

$$\text{Percent inhibition} = \left(\frac{A450\ OD \text{ negative control} - A450\ OD \text{ sample}}{A450\ OD \text{ negative control}}\right) \times 100$$

$$S/N \text{ ratio} = \left(\frac{A450\ OD \text{ sample}}{A450\ OD \text{ negative control}}\right)$$

If the S/N ratio was less than or equal to 0.6, the sample was classified as positive for the presence of anti-BoHV-1 antibodies (i.e., the animal from which the serum was obtained was infected with BoHV-1). If the S/N ratio was greater than 0.7, the sample was classified as negative for anti-BoHV-1 antibodies (i.e., the animal from which the serum was obtained was not infected with BoHV-1). If the SN ratio was between 0.6-0.7, then the sample was classified as suspect.

Results

The results of the competitive ELISA are summarized in Table 4, which shows the assessed competitive/blocking ELISA results of calf serum samples prior to infection (0 day) or at 28 days post infection (28 day) where the sera were obtained from BoHV-1 wt, BoHV-1 gEΔ and BoHV-1 tmv infected/vaccinated calves. The S/N ratio and % inhibition values shown in Table 4 were calculated from mean O.D of three replicate ELISA tests for each scrum samples are shown.

TABLE 4

Serological Competitive ELISA Results

| Groups | Samples | % Inhibition | | S/N Ratio | | Positive? |
|---|---|---|---|---|---|---|
| Neg. Control | FBS | 0 | | 1 | | N |
| Pos. Control | BoHV-1-HI | 71.02 | | 0.290 | | Y |
| | | 0 Day | 28 Day | 0 Day | 28 Day | |
| BoHV-1 WT | 2309 | 10.29 | 44.88 | 0.897 | 0.551 | Y |
| | 2349 | 19.21 | 41.29 | 0.808 | 0.587 | Y |
| | 2559 | 19.66 | 29.66 | 0.803 | 0.703 | Suspect |
| BoHV-1 gEΔ | 26 | 15.84 | 27.30 | 0.842 | 0.727 | N |
| | 27 | 13.85 | 31.48 | 0.862 | 0.685 | Suspect |
| | 28 | 6.49 | 18.99 | 0.935 | 0.810 | N |
| | 32 | 1.47 | 15.49 | 0.985 | 0.845 | N |
| BoHV-1 TMV | 31 | 3.93 | 8.72 | 0.961 | 0.913 | N |
| | 33 | 9.35 | 10.16 | 0.906 | 0.898 | N |
| | 369 | 2.00 | 14.97 | 0.980 | 0.850 | N |
| | 379 | 13.40 | 15.40 | 0.866 | 0.846 | N |
| | 385 | 10.16 | 10.96 | 0.898 | 0.890 | N |

In these competitive ELISA tests, day 0 sera obtained prior to infection from all three calves were negative for anti-BoHV-1 antibodies (SN ratio >0.7). Two of the three BoHV-1 wt infected calves were positive for anti-BoHV-1 antibodies (SN ratio <0.6). However, sera from one BoHV-1 wt infected calf had a somewhat higher SN ratio (SN ratio 0.7) (Table 4).

The ELISA test results also showed that three out of four calves infected with the commercially available gE-deleted virus tested negative at 28 dpi while one had a slightly lower SN ratio (0.685).

However, all five calves infected with BoHV-1 tmv tested negative in the competitive ELISA at both day 0 and 28 days post-infection.

Statistical analysis revealed that there was an overall significant interaction for Sample*DPI (p=0.021) with respect to SN Ratio. Post hoc comparisons indicated that there were significant differences on day 28 post-infection between the BoHV-1 wt-infected versus BoHV-1 gE ($p=0.0006$) and BoHV-1 tmv ($p=0.0025$) viruses-infected calves.

REFERENCES

1. Jones C, Chowdhury S: Bovine herpesvirus type 1 (BHV-1) is an important cofactor in the bovine respiratory disease complex. *Vet Clin North Am Food Anion Pract,* 26(2):303-321.
2. Jones C, Chowdhury S: A review of the biology of bovine herpesvirus type 1 (BHV-1), its role as a cofactor in the bovine respiratory disease complex and development of improved vaccines. *Anim Health Res Rev* 2007, 8(2):187-205.
3. Koppers-Lalic D, Reits E A, Ressing M E, Lipinska A D, Abele R, Koch J, Marcondes Rezende M, Admiraal P, van Leeuwen D, Bienkowska-Szewczyk K et al: Varicelloviruses avoid T cell recognition by UL49.5-mediated inactivation of the transporter associated with antigen processing. *Proc Natl Acad Sci USA* 2005, 102(14):5144-5149.
4. Nataraj C, Eidmann S, Hariharan M J, Sur J H, Pcrry G A, Srikumaran S: Bovine herpesvirus 1 downregulates the expression of bovine MHC class I molecules. *Viral Immunol* 1997, 10(1):21-34.
5. Chowdhury S I, Wci H, Wciss M, Pannhorst K, Paulsen D B: A triple gene mutant of BoHV-1 administered intranasally is significantly more efficacious than a BoHV-1 glycoprotein E-deleted virus against a virulent BoHV-1 challenge. *Vaccine* 2014, 32(39):4909-4915.
6. Butchi N B, Jones C, Perez S, Doster A, Chowdhury S I: Envelope protein Us9 is required for the anterograde transport of bovine herpesvirus type 1 from trigeminal ganglia to nose and eye upon reactivation. *J Neurovirol* 2007, 13(4):384-388.
7. Liu Z F, Brum M C, Doster A, Jones C, Chowdhury S I: A bovine herpesvirus type 1 mutant virus specifying a carboxyl-terminal truncation of glycoprotein E is defective in anterograde neuronal transport in rabbits and calves. *Journal of virology* 2008, 82(15):7432-7442.
8. Wei H, Wang Y, Chowdhury SI: Bovine herpesvirus type 1 (BHV-1) UL49.5 luminal domain residues 30 to 32 are critical for MHC-I down-regulation in virus-infected cells. *PloS one* 2011, 6(10):e25742.
9. Brum M C, Coats C, Sangena R B, Doster A, Jones C, Chowdhury S I: Bovine herpesvirus type 1 (BoHV-1) anterograde neuronal transport from trigeminal ganglia to nose and eye requires glycoprotein E. *J Neurovirol* 2009, 15(2):196-201.

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

The following statements summarize and describe aspects of the invention.

Statements:

1. An expression cassette or expression vector comprising a nucleic acid segment comprising or consisting essentially of a sequence with at least 95% sequence identity to SEQ ID NO:2 or 3.
2. An expression cassette or expression vector comprising a nucleic acid segment consisting of a sequence with at least 95% sequence identity to SEQ ID NO:2 or 3.
3. A host cell comprising the expression cassette or expression vector of statement 1 or 2.
4. A method of manufacturing a polypeptide or peptide comprising culturing a host cell comprising the expression cassette or expression vector of statement 1 or 2 while the host cell expresses the polypeptide or peptide from the expression cassette or expression vector.
5. The method of statement 4, wherein the polypeptide or peptide is an antigen.
6. A polypeptide or peptide comprising a sequence with at least 95% sequence identity to any of SEQ ID NO:1, 4-44, or 45.
7. A polypeptide or peptide comprising or consisting essentially of a sequence selected from SEQ ID NO:1, 4-44, or 45.
8. The polypeptide or peptide of statement 6 or 7, consisting of a sequence selected from SEQ ID NO:1, 4-44, or 45.
9. The polypeptide or peptide of any of statements 6-8, wherein the polypeptide or peptide is an antigenic polypeptide or peptide.
10. The polypeptide or peptide of any of statements 6-9, immobilized to a solid surface.
11. The polypeptide or peptide of any of statements 6-10, covalently attached to a label.
12. A composition comprising at least one polypeptide or peptide antigen comprising sequence with at least 95% sequence identity to any of SEQ ID NO:1, 4-44, or 45.
13. A composition comprising at least one polypeptide or peptide antigen comprising or consisting essentially of a sequence selected from SEQ ID NO:1, 4-44, or 45.
14. A composition comprising at least one polypeptide or peptide antigen consisting of a sequence selected from SEQ ID NO:1, 4-44, or 45.
15. The composition of any of statements 12-14, further comprising a carrier.
16. The composition of any of statements 12-15, formulated for administration to an animal.
17. An antibody that selectively binds to at least one polypeptide or peptide antigen comprising a sequence with at least 95% sequence identity to any of SEQ ID NO:1, 4-44, or 45.
18. An antibody that selectively binds to at least one polypeptide or peptide antigen comprising or consisting essentially of a sequence selected from SEQ ID NO:1, 4-44, or 45.
19. A antibody that selectively binds to an epitope within at least one polypeptide or peptide antigen comprising or consisting essentially of a sequence selected from SEQ ID NO:1, 4-44, or 45.

20. A antibody that selectively binds to at least one polypeptide or peptide antigen that comprises an epitope consisting of a sequence selected from SEQ ID NO:1, 4-44, or 45.

21. A device comprising a solid surface and at least one polypeptide or peptide comprising or consisting essentially of a sequence with at least 95% sequence identity to any of SEQ ID NO:1, 4-44, or 45.

22. A device comprising a solid surface and at least one polypeptide or peptide antigen comprising or consisting essentially of a sequence selected from SEQ ID NO:1, 4-44, or 45.

23. A device comprising a solid surface and at least one polypeptide or peptide antigen consisting of a sequence selected from SEQ ID NO:1, 4-44, or 45.

24. The device of any of statements 21-23, where the solid surface comprises a chip, strip, paper, microliter plate, bead, test tube, slide, or filter.

25. The device of any of statements 21-24, where the solid surface comprises glass, plastic, cellulose, ethylcellulose, methylcellulose, paper, nitrocellulose, hydroxypropylcellulose, hydroxypropyl methylcellulose, polystyrene, polyethylene, lipid polydiacetylene (PDA), polydimethylsiloxane, nylon, rayon, cotton, teflon, mica, sephadex, sepharose, polyacrylonitrile, glass-fiber paper, gold, silicon, silica, or combinations thereof 26. A device comprising a solid surface and at least antibody that selectively binds to at least one polypeptide or peptide antigen comprising a sequence with at least 95% sequence identity to any of SEQ ID NO:1, 4-44, or 45.

27. A device comprising a solid surface and at least antibody that selectively binds to at least one polypeptide or peptide antigen comprising or consisting essentially of a sequence selected from SEQ ID NO:1, 4-44, or 45.

28. A device comprising a solid surface and at least antibody that selectively binds to at least one polypeptide or peptide antigen consisting of a sequence selected from SEQ ID NO:1, 4-44, or 45.

29. The device of any of statements 26-28, where the solid surface comprises a chip, strip, paper, microliter plate, bead, test tube, slide, or filter.

30. The device of any of statements 26-29, where the solid surface comprises glass, plastic, cellulose, ethylcellulose, methylcellulose, paper, nitrocellulose, hydroxypropylcellulose, hydroxypropyl methylcellulose, polystyrene, polyethylene, lipid polydiacetylene (PDA), polydimethylsiloxane, nylon, rayon, cotton, teflon, mica, sephadex, sepharose, polyacrylonitrile, glass-fiber paper, gold, silicon, silica, or combinations thereof.

31. A method comprising:
    (a) contacting a test sample with at least one polypeptide or peptide to form an assay mixture, where the at least one polypeptide or peptide comprises or consists essentially of a sequence with at least 95% sequence identity to any of SEQ ID NO:1, 4-44, or 45; and
    (b) detecting or measuring whether a complex between the at least one polypeptide or peptide and antibodies is present in the assay mixture.

32. A method comprising:
    (a) applying a test sample to a device comprising a solid surface and at least one polypeptide or peptide to form an assay mixture, where the at least one polypeptide or peptide comprises or consists essentially of a sequence with at least 95% sequence identity to any of SEQ ID NO:1, 4-44, or 45; and
    (b) detecting or measuring whether a signal from the assay mixture indicates that antibodies are present in the test sample.

33. A method comprising:
    (a) applying a test sample to a device comprising a solid surface and an antibody that selectively binds to at least one polypeptide or to form an assay mixture, where the at least one polypeptide or peptide comprises or consists essentially of a sequence with at least 95% sequence identity to any of SEQ ID NO:1, 4-44, or 45; and
    (b) detecting or measuring whether a signal from the assay mixture indicates that at least one of the polypeptides or the peptide antigens are present in the test sample.

34. The method of any of statements 31-33, wherein the at least one polypeptide or peptide is a polypeptide antigen or a peptide antigen.

35. The method of any of statement 31-34, wherein the at least one polypeptide or peptide comprises or consists essentially of a sequence selected from SEQ ID NO:1, 4-44, or 45.

36. The method of any of statement 31-35, the polypeptide or peptide consists of a sequence selected from SEQ TD NO:1, 4-44, or 45.

37. The method of any of statements 32-36, where the solid surface comprises a chip, strip, paper, microliter plate, bead, test tube, slide, gel, or filter.

38. The method of any of statements 32-37, where the solid surface comprises glass, plastic, cellulose, ethylcellulose, methylcellulose, paper, nitrocellulose, hydroxypropylcellulose, hydroxypropyl methylcellulose, polystyrene, polyethylene, lipid polydiacetylene (PDA), polydimethylsiloxane, polyacrylamide, nylon, rayon, cotton, teflon, mica, sephadex, sepharose, polyacrylonitrile, glass-fiber paper, gold, silicon, silica, or combinations thereof 39. The method of any of statements 31-38, where detecting or measuring comprises contacting the polypeptide, peptide, antibody, or a combination thereof with a binding entity.

40. The method of statement 39, where the binding entity comprises at least one label.

41. The method of statement 39 or 40, where the binding entity comprises at least one label that emits a detectable signal.

42. The method of any of statements 38-41, where the at least label is selected from an enzyme, a fluorophore, chromophore, radioisotope, enzymatic substrate, enzymatic tag, antibody, chemiluminescent molecule, electroluminescent molecule, magnetism, electron transmitter, electron dense molecule, affinity label, or a combination thereof.

43. The method of any of statements 31-42, where detecting or measuring comprises measuring an amount of color, enzymatic product, radioactivity, chemiluminescence, electroluminescence, electricity, or a combination thereof.

44. The method of any of statements 31-43, where detecting or measuring comprises measuring optical density of at least a portion of the device (or the solid surface).

45. The method of any of statements 31-44, where detecting or measuring comprises measuring an optical density or more than one optical density.

46. The method of any of statements 31-45, where detecting or measuring comprises measuring the optical density of at least one test sample assay to produce a test sample optical density, and comparing the test sample optical density to an optical density of one or more negative control.

47. The method of any of statements 31-45, where detecting or measuring a signal comprises measuring the optical density of at least one test sample to produce a test sample optical density, and comparing the test sample optical density to an optical density of one or more negative control using one or both of the following algorithms:

$$\text{Percent inhibition} = \left(\frac{OD \text{ negative control} - OD \text{ sample}}{OD \text{ negative control}}\right) \times 100$$

$$S/N \text{ ratio} = \left(\frac{OD \text{ sample}}{OD \text{ negative control}}\right).$$

48. A kit comprising a instructions for use of the kit components, and any of the following separately packaged components:
   (a) at least one polypeptide or peptide comprising or consisting essentially of a sequence with at least 95% sequence identity to any of SEQ ID NO:1, 4-44, or 45;
   (b) a binding entity that specifically binds to at least one polypeptide or peptide comprising or consisting essentially of a sequence with at least 95% sequence identity to any of SEQ ID NO:1, 4-44, or 45;
   (c) a secondary binding entity that specifically binds to at least one polypeptide or peptide comprising or consisting essentially of a sequence with at least 95% sequence identity to any of SEQ ID NO:1, 4-44, or 45;
   (d) a label or a reagent for developing a signal from a label; or
   (e) any combination thereof.

49. A kit comprising the device of any of statements 21-30, and instructions for using the device.

50. The kit of statement 48, comprising a series of devices.

51. The kit of statement 48 or 49, wherein each device is separately and/or sterilely packaged.

The specific methods, compositions, devices, and kits described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims.

As used herein and in the appended claims, the singular forms "a," "an," and "the" include plural reference unless the context clearly dictates otherwise. Thus, for example, a reference to "an antigen" or "an antibody" includes a plurality (for example, a solution of antigens, a solution of antigens, a solution of antibodies or a series of antibody preparations) of such antigens or antibodies, and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method comprising:
   (a) contacting a test sample from an animal with at least one polypeptide or peptide to form an assay mixture, where the at least one polypeptide or peptide is selected from the group consisting of a polypeptide or peptide comprising an N-terminal six histidine tag and a sequence segment with at least 95% sequence identity to a sequence of SEQ ID NO:1, and a polypeptide or peptide comprising the sequence segment of SEQ ID NO:4; and
   (b) detecting or measuring whether a complex between the at least one polypeptide or peptide and antibodies is present in the assay mixture.

2. The method of claim 1, further comprising determining whether said animal is infected with a Bovine herpesvirus type 1 (BoHV-1), vaccinated with a recombinant BoHV-1 triple mutant virus (BoHV-1 tmv), or uninfected with a Bovine herpesvirus type 1 (BoHV-1), at least in part from said detecting or measuring whether a complex between the at least one polypeptide or peptide and antibodies is present in the assay mixture.

3. The method of claim 1, wherein the at least one polypeptide or peptide is immobilized on a solid surface.

4. The method of claim 3, where the solid surface comprises a chip, strip, paper, microtiter plate, bead, test tube, slide, gel, or filter.

5. The method of claim 3, where the solid surface comprises glass, plastic, cellulose, ethylcellulose, methylcellulose, paper, nitrocellulose, hydroxypropylcellulose, hydroxypropyl methylcellulose, polystyrene, polyethylene, lipid polydiacetylene (PDA), polydimethylsiloxane, polyacrylamide, nylon, rayon, cotton, teflon, mica, sephadex, sepharose, polyacrylonitrile, glass-fiber paper, gold, silicon, silica, or combinations thereof.

6. The method of claim 1, where detecting or measuring comprises contacting the complex, or a polypeptide, a peptide, or an antibody in the complex with a binding entity.

7. The method of claim 6, where the binding entity comprises at least one label.

8. The method of claim 6, where the binding entity comprises at least one label that emits a detectable signal.

9. The method of claim 8, where the at least label is selected from an enzyme, fluorophore, chromophore, radioisotope, enzymatic substrate, enzymatic tag, antibody, chemiluminescent molecule, electroluminescent molecule, magnetism, electron transmitter, electron dense molecule, affinity label, or a combination thereof.

10. The method of claim 1, where detecting or measuring comprises measuring an amount of color, enzymatic product, radioactivity, chemiluminescence, electroluminescence, electricity, or a combination thereof.

11. The method of claim 1, where detecting or measuring comprises measuring optical density.

12. The method of claim 1, where detecting or measuring comprises measuring optical density of the assay mixture, or a signal produced by a label present in the assay mixture.

13. The method of claim 1, where detecting or measuring comprises measuring the optical density of at least one assay mixture to produce an assay mixture optical density, and comparing the assay mixture optical density to an optical density of one or more negative control, one or more positive control, or both.

14. The method of claim 1, where detecting or measuring comprises measuring the optical density of at least one assay mixture to produce an assay mixture optical density, and comparing the assay mixture optical density to an optical density of one or more negative control using one or both of the following algorithms:

$$\text{Percent inhibition} = \left(\frac{OD \text{ negative control} - OD \text{ sample}}{OD \text{ negative control}}\right) \times 100$$

$$S/N \text{ ratio} = \left(\frac{OD \text{ sample}}{OD \text{ negative control}}\right)$$

wherein:
   OD negative control is the optical density of the negative control; and
   OD sample is the optical density of the assay mixture optical density.

15. The method of claim 1, wherein the at least one polypeptide or peptide is a polypeptide or peptide comprising an N-terminal six histidine tag and a sequence segment with at least 95% sequence identity to a sequence of SEQ ID NO:1.

16. The method of claim 1, wherein the at least one polypeptide is a polypeptide or peptide comprising the sequence segment of SEQ ID NO:4.

17. An expression cassette or expression vector comprising a nucleic acid segment encoding a polypeptide or peptide selected from the group consisting of a polypeptide or peptide comprising an N-terminal six histidine tag and a sequence segment with at least 95% sequence identity to a sequence of SEQ ID NO:1, and a polypeptide or peptide comprising the sequence segment of SEQ ID NO:4.

18. A kit comprising any of the following separately packaged components:
   (a) at least one polypeptide or peptide selected from the group consisting of a polypeptide or peptide comprising an N-terminal six histidine tag and a sequence segment with at least 95% sequence identity to a sequence of SEQ ID NO:1, and a polypeptide or peptide comprising the sequence segment of SEQ ID NO:4;
   (b) a binding entity that specifically binds to said at least one polypeptide or peptide;

(c) a secondary binding entity that specifically binds to said at least one polypeptide or peptide;
(d) a label or a reagent for developing a signal from a label;
(e) a device comprising a solid surface and at least one polypeptide or peptide comprising a sequence selected from the group consisting of SEQ ID NO:4 and a polypeptide or peptide comprising an N-terminal six histidine tag and a sequence segment with at least 95% sequence identity to a sequence of SEQ ID NO:1; or
(f) any combination thereof.

19. The kit of claim 18, further comprising instructions for use of the kit components.

* * * * *